United States Patent [19]

Gries et al.

[11] Patent Number: 4,963,344
[45] Date of Patent: * Oct. 16, 1990

[54] METHOD TO ENHANCE NMR IMAGING USING CHELATED PARAMAGNETIC IONS

[75] Inventors: Heinz Gries; Douwe Rosenberg; Hann-Joachim Weinmann; Ulrich Speck; Wolfgang Mutzel, Georg-Alexander Hoyer; Heinrich Pfeiffer all of Berlin, Fed. Rep. of Germany

[73] Assignee: Schering Aktiengesellschaft, Berlin and Bergkamen, Fed. Rep. of Germany

[ * ] Notice: The portion of the term of this patent subsequent to Mar. 3, 2004 has been disclaimed.

[21] Appl. No.: 370,139

[22] Filed: Jun. 23, 1989

Related U.S. Application Data

[63] Continuation of Ser. No. 20,993, Mar. 2, 1987, abandoned, which is a continuation of Ser. No. 573,184, Jan. 23, 1984, Pat. No. 4,647,447, which is a continuation-in-part of Ser. No. 401,594, Jul. 26, 1982, abandoned.

[30] Foreign Application Priority Data

| Jul. 24, 1981 | [DE] | Fed. Rep. of Germany | ....... | 3129906 |
| Jan. 21, 1983 | [DE] | Fed. Rep. of Germany | ....... | 3302410 |
| Jan. 11, 1984 | [DE] | Fed. Rep. of Germany | ....... | 3401057 |

[51] Int. Cl.$^5$ ...................... H61K 49/00; G01N 31/00
[52] U.S. Cl. ................ 424/9; 128/653 CA; 128/654; 436/173; 436/806
[58] Field of Search ..................... 424/9; 128/653, 654; 436/173, 806

[56] References Cited

U.S. PATENT DOCUMENTS

| 3,832,457 | 8/1974 | Sugimoto et al. | 424/4 |
|---|---|---|---|
| 4,017,596 | 4/1977 | Loberg et al. | |
| 4,125,599 | 11/1978 | Wiegert | 424/5 |
| 4,167,564 | 9/1979 | Jensen | 424/177 |
| 4,206,132 | 6/1980 | Sievers | 260/429.2 |
| 4,310,507 | 1/1982 | Luckey | 424/4 |
| 4,352,751 | 10/1982 | Wieder et al. | 260/112 R |
| 4,432,907 | 2/1984 | Weider et al. | 260/429.2 |
| 4,454,106 | 6/1984 | Gansow et al. | 424/1.1 |
| 4,472,509 | 9/1984 | Gansow et al. | 436/548 |
| 4,478,816 | 10/1984 | Ledley et al. | 424/4 |
| 4,615,879 | 10/1986 | Runge et al. | 424/9 |
| 4,671,958 | 6/1987 | Rodwell et al. | 424/85 |
| 4,731,239 | 3/1988 | Gordon | 424/9 |
| 4,741,900 | 5/1988 | Alvarez et al. | 424/85 |

FOREIGN PATENT DOCUMENTS

| 0008174 | 2/1980 | European Pat. Off. . |
|---|---|---|
| 0055028 | 6/1982 | European Pat. Off. . |
| 0063949 | 11/1982 | European Pat. Off. . |
| 0065347 | 11/1982 | European Pat. Off. . |
| 0071564 | 2/1983 | European Pat. Off. . |
| 2527158 | 12/1976 | Fed. Rep. of Germany . |
| 2918842 | 12/1979 | Fed. Rep. of Germany . |
| 1111504 | 3/1956 | France . |
| 837234 (484M) | 5/1961 | France . |
| 845624 (988M) | 12/1961 | France . |
| 2322586 | 4/1977 | France . |
| 736432 | 9/1955 | United Kingdom . |
| 1273446 | 5/1972 | United Kingdom . |
| 1366352 | 9/1974 | United Kingdom . |
| 1398276 | 6/1975 | United Kingdom . |
| 1399368 | 7/1975 | United Kingdom . |
| 1405372 | 9/1975 | United Kingdom . |
| 1435967 | 5/1976 | United Kingdom . |
| 1461250 | 1/1977 | United Kingdom . |
| 1466969 | 3/1977 | United Kingdom . |
| 1497904 | 1/1978 | United Kingdom . |
| 1504243 | 3/1978 | United Kingdom . |
| 1522103 | 8/1978 | United Kingdom . |
| 1525418 | 9/1978 | United Kingdom . |
| 2001969A | 2/1979 | United Kingdom . |
| 2008944A | 6/1979 | United Kingdom . |
| 2019397A | 10/1979 | United Kingdom . |
| 1565186 | 4/1980 | United Kingdom . |
| 1584787 | 2/1981 | United Kingdom . |
| 2060623A | 5/1981 | United Kingdom . |
| 1594109 | 7/1981 | United Kingdom . |
| 1598610 | 9/1981 | United Kingdom . |
| 1599256 | 9/1981 | United Kingdom . |
| 2109407A | 6/1983 | United Kingdom . |

OTHER PUBLICATIONS

J. F. Desreux, "Nuclear Magnetic Resonance Spectroscopy of Lanthanide Complexes with a Tetraactic Tetraaza Macrocycle, Unusual Conformation Properties," Inorg. Chem., 1980, 19, 1319-1324.

A. E. Martell and M. Calvin, Chemistry of the Metal Chelate Compounds, Prentice-Hall: New York, 1952, pp. ix-xi, 184-184, 207-224, 514-558.

Rubin et al., "The Metabolism of Parenteral Iron Chelates", Biochemical Medicine, vol. 3, pp. 271-288, (1970).

Chemical Abstract, 103:30580b, (Duesler et al.).

The Merck Index, 10th Ed., pp. 578-580, (1983).

Gore et al., "Relaxation Rate Enhancement Observed In Vivo by NMR Imaging" in Partain et al., (eds.), Nuclear Magnetic Resonance (NMR) Imaging, Philadelphia, WB Saunders, Co., 1983.

(List continued on next page.)

Primary Examiner—Richard L. Raymond
Attorney, Agent, or Firm—Millen, White & Zelano

[57] ABSTRACT

Agents useful for influencing the relaxation times in NMR diagnostics, contain at least one paramagnetic, physiologically compatible complex salt comprising a chelate from an open-chain or cyclic complex-forming compound containing organic nitrogen, phosphorus, oxygen and/or sulfur, and a complexed ion of the lanthanide elements of atomic number 57-70 or of the transition metals of atomic numbers 21-29, 42 and 44, and, optionally, an inorganic or organic base or acid.

169 Claims, No Drawings

OTHER PUBLICATIONS

Chauncey et al., "Tissue Distribution Studies with Radioactive Manganese: A Potential Agent for Myocardial Imaging", Jour. of Nuc. Med., vol. 18, pp. 933-966, 1977.

Herman et al., "Three-Dimensional Display of Nuclear Magnetic Resonance Images", Optical Engineering, vol. 21, No. 5, pp. 923-926, Sep./Oct. 1982.

Frank et al., "Measurement of Proton Nuclear Magnetic Longitudinal Relaxation Times and Water Content in Infracted Canine Myocardium and Induced Pulmonary Injury", Clinical Research, vol. 24, p. 217A, 1976.

P. C. Lauterbur et al., "Augmentation of Tissue Water Proton Spin-Lattice Relaxation Rates by In Vivo Addition of Paramagnetic Ions", Frontiers of Biological Energetics, vol. 1, 752-759, (Encl. 2).

Doyle, F. H., et al., "Relaxation Rate Enhancement Observed In Vivo by NMR Imaging", Proceedings of NMR Imaging Symposium held in Nashville, Tenn., on Oct. 26-27, 1980, and abstracted on Journal of Computer Assisted Tomography, 5 (2) 295-296.

Lauterbur, P. C., "Progress in NMR Zeugmatographic Imaging", Phil. Trans. R. Soc. Lond. B 298, 483-87, (1980).

Pykett, Ian L., "Nuclear Magnetic Resonance, or NMR, Can Reveal the Distribution of Atoms in a Sample of Material. It Can Do the Same in the Body, Generating Images of Internal Structure Without the Use of X Rays", NMR Imaging in Medicine, pp. 78-88.

Brady et al., Radiology, 144, 343, (1982).

Young et al., J. Comput. Tomography 5,6:543-46, (1981).

Morgan et al., "Proton Spin Relaxation in Aqueous Solutions of Paramagnetic Ions. II. $Cr^{+++}$, $Ni^{++}$, $Cu^{++}$, and $Gd^{+++}$," The Journal of Chemical Physics, vol. 31, No. 2, pp. 365-368, (Aug. 1959).

Eisinger et al., "Transition Metal Binding in DNA Solutions," The Journal of Chemical Physics, vol. 36, No. 7, pp. 1721-1729, (04/01/1962).

Bertinchamps et al., "Interdependence of Routes Excreting Manganese," Am. J. of Physiology, 211(1), pp. 217-224, (1966).

Catsch, "Probleme de Chelat-Therapie," Naturwissenschaften, pp. 473-474, (1968).

Hosain et al., "Ytterbium-169 Diethylenetriaminepentaacetic Acid Complex," Radiology, 91, pp. 1199-1203, (Dec. 1968).

Davies, "The Clinical Significance of the Essential Biological Metals," Chapter 4—Manganese, pp. 69-80, (London, 1972).

Dwek, "Proton Relaxation Enhancement Probes," Advances in Molecular Relaxation Processes, 4, pp. 1-53, (1972).

Levy et al., "Paramagnetic Relaxation Reagents: Alternatives or Complements to Lanthanide Shift Reagents in Nuclear Magnetic Resonance Spectral Analysis," J. of Am. Chem. Soc., 96:3, pp. 678-681, (02/06/1974).

Derwent Abstract, 61698V/35, (Aug. 22, 1974).

Derwent Abstract, 135A/020, (1975).

Derwent Abstract, 07413x/04, (Jan. 13, 1976).

Ovitt et al., "Improved Instrumentation and Techniques for Non-Invasive Detection, Characterization and Quantification of Arteriosclerosis for Research and Diagnostic Purposes," NTIS No. PB-268,227, dated Apr. 1976.

Chemical Abstract, vol. 87:1879b, Loberg et al., (1977).

Derwent Abstract 84974X/46, (Oct. 29, 1976).

Derwent Abstract, 221/170, (1977).

Elgavish et al. (I), "Aqueous Lanthanide Shift Reagents: 3. Interaction of Ethylenediaminetetraacetate Chelates with Substituted Ammonium Cations," J. Am. Chem. Soc., 99:6, pp. 1762-1765, (03/16/1977).

Ovitt et al., "Improved Instrumentation and Techniques for Non-Invasive Detection, Characterization and Quantification of Atherosclerosis for Research and Diagnostic Purposes," NTIS No. PB-272,617, dated May 1977.

Rote Liste, 1977/78, 12 Antidota, p. 12001.

Lauterbur et al., "Augmentation of Tissue Water Proton Spin-Lattice Relaxation Rates by In Vivo Addition of Paramagnetic Ions," Frontiers of Biological Energetics, vol. 1, pp. 752-759, (1978).

Chemical Abstracts, vol. 91:133246k, Carmona et al., (1979).

Derwent Abstract, 150/429, (1979).

Derwent Abstract, 144/005, (1979).

Derwent Abstract, 78609B/43, (Jan. 30, 1979).

Burton et al., "Proton Relaxation Enhancement (PRE) in Biochemistry: A Critical Survey," *Progress in NMR Spectroscopy*, vol. 13, pp. 1-45, (1979).

Derwent Abstract, 23893B/12, (Mar. 13, 1979).

Ovitt et al., "Improved Instruments and Techniques for Non-Invasive Detection, Characterization and Quantification of Atherosclerosis for Research and Diagnostic Purposes," NTIS No. PB82-118688, dated Sep. 1, 1979.

Derwent Abstract, 81534B/45, (Sep. 29, 1979).

Lauterbur, "Progress in NMR Zeugmatographic Imaging," Phil. Trans. R. Soc. Lond., B. 289, pp. 483-487, (1980).

Chemical Abstracts, vol. 93:81186k, (1980), Nozaki et al.

Dechter et al., "Aqueous Relaxation Reagents in Nitrogen-15 NMR," *Journal of Magnetic Resonance*, 39, pp. 207-215, (1980).

Forsberg et al., "Gmelin Handbuch der Anorganischen Chemie: Sc, Y, La-Lu, Rare Earth Elements," 8th Ed., Springer-Verlag, New York, pp. 198-204, (1980).

Derwent Abstract, 05092C/03, (Jan. 1, 1980).

Chemical Abstract, vol. 93:31813s, (Jan. 29, 1980).

Derwent Abstract, 02446D/03, (Jan. 7, 1981).

Chemical Abstract, vol. 95:38681x, Wieder et al., (1981).

Derwent Abstract, 29038D/16, (Apr. 2, 1981).

Derwent Abstract, 34726D/20, (May 6, 1981).

Cotzias, "Manganese versus Magnesium: Why are they so Similar in Vitro and so Different in Vivo?", Brookhaven Nat'l Laboratory, Upton, N.Y., pp. 98-103.

Derwent Abstract, 124/026, (1981).

Tyler et al., "In Vivo Enhancement of Ultrasonic Image Luminence by Aqueous Solutions with High (List continued on next page.)

OTHER PUBLICATIONS

Speed of Sound, Ultrasonic Imaging," pp. 323-329, (1981).

Young et al., "Enhancement of Relaxation Rate with Paramagnetic Contrast Agents in NMR Imaging," Journal of Computer Assisted Tomography, vol. 5, No. 6, pp. 543-546, (1981).

Doyle et al., "Relaxation Rate Enhancement Observed in Vivo by NMR Imaging," Journal of Computer Assisted Tomography, vol. 5, No. 2, pp. 295-296, (1981).

Pykett, "NMR Imaging in Medicine," Scientific American, 246, pp. 78-88, (1982).

Chemical Abstracts, vol. 96:115204u, (1982).

Brady et al., "Proton Nuclear Magnetic Resonance Imaging of Regional Ischemic Canine Hearts: Effect of Parametric Proton Signal Enhancement," Radiology: 144, pp. 343-347, (Jul. 1982).

Mendonca-Dias et al., "Paramagnetic Contrast Agents in Nuclear Magnetic Resonance Medial Imaging," Seminars in Nuclear Medicine, vol. XIII, No. 4, pp. 364-376 (Oct. 1983).

Brasch et al., "Contrast-Enhanced NMR Imaging: Animal Studies Using Gadolinium-DTPA Complex," AJR 142, pp. 625-630 (Mar. 1984).

Weinmann et al., "Characteristics of Gadolinium-DTPA Complex: A Potential NMR Contrast Agent," AJR 142, pp. 619-624 (Mar. 1984).

Carr et al., "Intravenous Chelated Gadolinium as a Contrast Agent and NMR Imaging of Cerebral Tumors," The Lancet (Mar. 3, 1984).

Runge et al., "Work in Progress: Potential Oral and Intravenous Paramagnetic NMR Contrast Agents," Radiology 147:789-791 (6/1983).

Hansen et al., "In Vivo Imaging of the Rat Anatomy with Nuclear Magnetic Resonance," Radiology 136:695-700 (Sep. 1980).

Durbin et al., "Metabolism of the Lanthanons in the Rat," Proc. Soc. Exp. Biol., 91, pp. 78-85 (1956).

Pople et al., *High-Resolution Nuclear Magnetic Resonance*, p. 209 (1959).

Graca et al., Comparative Toxicity of Stable Rare Earth Compounds," Arch. Environ. Health 5:437-444 (Nov. 1962).

Graca et al., "Comparative Toxicity of Stable Rare Earth Compounds," Arch. Environ. Health 8:555-564 (Apr. 1964).

Hollis et al., "Effect of Manganese Ion on the Phosphorus Nuclear Magnetic Resonance Spectra of the Perfused Rabbit Heart: A Possible New Clin. Res." 26:240A (1979).

Moeller, *Comprehensive Inorganic Chemistry*, vol. 4, "The Lanthanides," pp. 10-13.

Sovak [Amiel, (ed.)], "Futurology of Contrast Media: A Partially Warranted Prophecy," *Contrast Media in Radiology*, pp. 329-335 (Sep. 1981).

Goldman et al. (I), [Witcofski et al. (eds.)], "Cardiac Applications of NMR Imaging" in *NMR Imaging: Proceedings of International Symposium of Nuclear Magnetic Resonance Imaging*, Bowman Gray School of Medicine of Wakeforest Univ., N.C., Oct. 1-3, 1981, pp. 171-173.

Wenzel et al., "Water Soluble Paramagnetic Relaxation Reagents for Carbon-13 Nuclear Magnetic Resonance Spectrometry,+ Analytical Chem. 54:4, pp. 615-621 (Apr. 1982).

Alfidi et al., "Preliminary Experimental Results in Humans and Animals with a Superconducting, Whole Body, Nuclear Magnetic Resonance Scanner," Radiology 143:175-181 (Apr. 1982).

Chemical Abstracts, vol. 97:29690z, Bryden et al. (1982).

Brasch et al. (I), "NSFR: NMR Contrast Agent for the CNS," Symposium Neuroradiologicum, Washington, D.C., Oct. 1982.

Goldman et al. (II), "Quantification of Experimental Myocardial Infarction Using Nuclear Magnetic Resonance Imaging and Paramagnetic Ion Contrast Enhancement in Excised Canine Hearts," Circulation 66(5), pp. 1012-1016 (Nov. 1982).

Brasch et al. (II), "Work in Progress: Nuclear Magnetic Resonance Study of a Paramagnetic Nitroxide Contrast Agent for Enhancement of Renal Structures in Experimental Animals," Radiology 147, pp. 773-779 (Jun. 1983).

Chemical Abstract 99:49843k (1983), Runge et al.

Yellon et al., "Temporal and Spatial Characteristics of Evolving Cell Injury During Regional Myocardial Ischemia in the Dog: The Border Zone Controversy," JACC, vol. 2, No. 4, pp. 661-670 (Oct. 1983).

Runge et al., "Paramagnetic Agents for Contrast-Enhanced NMR Imaging: A Review," AJR 141, pp. 1209-1215 (Dec. 1983).

Mansfield et al., "NMR Imaging in Biomedicine," *Advances in Magnetic Resonance*, Supplement 2, pp. 232-235 (1982).

Horrocks et al., "Lanthanide Porphyrin Complexes. Evaluation of Nuclear Magnetic Resonance Dipolar Probe and Shift Reagent Capabilities," J. Am. Chem. Soc., 98:23, pp. 7157-7162 (Nov. 10, 1976).

Shapiro et al., "Heavy-Metal Chelates and Cesium Salts for Contrast Radiography," Annals New York Academy of Sciences, pp. 756-763 (1959).

Gansow et al., "Snythesis and Chemical Properties of Lanthanide Cryptates," J. Am. Chem. Soc. 99:21, pp. 7087-7089 (Oct. 12, 1977).

Elgavish et al. (II), "Aqueous Lanthanide Shift Reagents. 1. Interaction of the Ethylenediaminetetraacetate Chelates With Carboxylates. pH Dependence, Ionic Medium Effects, and Chelate Structure," J. Am. Chem. Soc., 98:16, pp. 4755-4759 (Aug. 4, 1976).

Kaufman et al., *Nuclear Magnetic Resonance Imaging in Medicine*, Igaku-Shoin Medical Publishers, Inc. (New York), pp. vii-x, 7 (1981).

Krejcarek et al., "Covalent Attachment of Chelating Groups to Macromolecules," Biochemical and Biophysical Research Communications, vol. 77, No. 2, pp. 581-585 (1977).

Ellis, "The Lanthanide Elements in Biochemistry, Biology and Medicine," Inorganic Perspectives in Biology and Medicine, 1, pp. 101-135 (1977).

Wieder et al., Chem. Abstracts 95:38681x (1981).

Bydder et al., "Clinical NMR Imaging of the Brain: 140 Cases," AJR:139, pp. 215-236 (Aug. 1982).

Gore et al., "Nuclear Magnetic Resonance (NMR) Imaging at Hammersmith Hospital," SPIE vol. 273, Application of Optical Instrumentation in Medicine IX (1981), pp. 8-10.

Article 115 of EPC filing paper (Dec. 4, 1984).

Dwyer et al., *Chelating Agents and Metal Chelates*, pp. 388-400, Academic Press, Inc., New York (1964).

Translation of Catsch, "Probleme der Chelat-Therapie," Naturwissenschaften, pp. 473-474 (1968).

METHOD TO ENHANCE NMR IMAGING USING CHELATED PARAMAGNETIC IONS

CROSS-REFERENCE TO RELATED APPLICATIONS

This is a continuation application of Ser. No. 020,993, filed Mar. 2, 1987, now abandoned, which is a continuation application of Ser. No. 573,184, filed Jan. 23, 1984, now U.S. Pat. No. 4,647,447, which is a continuation in part of Ser. No. 401,594, filed July 26, 1982, now abandoned, and is related to Federal Republic of Germany Application No. 33 02 410.3 filed Jan. 21, 1983, the latter two applications being entirely incorporated by reference herein.

BACKGROUND OF THE INVENTION

Complexes or their salts have long been used in medicine, for example, as aids in administering poorly soluble ions (e.g., iron) and as antidotes (in which calcium or zinc complexes are preferred) for detoxification in cases of inadvertent bodily incorporation of heavy metals or their radio isotopes.

SUMMARY OF THE INVENTION

It is an object of this invention to provide complex salts for use in valuable diagnostic techniques.

Upon further study of the specification and appended claims, further objects and advantages of this invention will become apparent to those skilled in the art.

It has now been found that physiologically well tolerated complex salts formed from the anion of a complexing acid and one or more central ions of an element with an atomic number of 21 to 29, 42, 44 or 57 to 83 and, optionally, also fomred from one or more physiologically biocompatible cations of an inorganic and/or organic base or amino acid, surprisingly are suitable for producing diagnostic media which are suitable for use in NMR, X-ray and/or ultrasonic diagnosis.

Thus, these objects have been attained by providing, preferably, a diagnostic medium containing at least one physiologically well tolerated complex salt of the formulae I or II

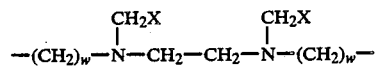

(I)

or

N(CH$_2$X)$_3$, (II)

wherein, X is —COOY, —PO$_3$HY or —CONHOY; Y is a hydrogen atom, a metal ion equivalent and/or a physiologically biocompatible cation of an inorganic or organic base or amino acid, A is —CHR$_2$—CHR$_3$—, —CH$_2$—CH$_2$(ZCH$_2$—CH$_2$)$_m$—,

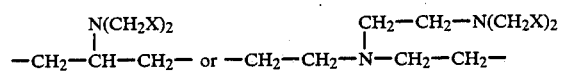

wherein X is defined as above, each R$_1$ is hydrogen or methyl, R$_2$ and R$_3$ together represent a trimethylene group or a tetramethylene group or individually are hydrogen atoms, lower alkyl groups (e.g., 1–8 carbon atoms), phenyl groups, benzyl groups, or R$_2$ is a hydrogen atom and R$_3$ is —(CH$_2$)$_p$—C$_6$H$_4$—W—protein wherein p is 0 or 1, W is —NN—, —NHCOCH$_2$— or —NHCS—, -protein represents a protein residue, m is the number 1, 2 or 3, Z is an oxygen atom or a sulfur atom or the group

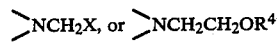

wherein X is as defined above and R$_4$ is a lower alkyl group (e.g., 1–8 carbon atoms), V has the same meaning as X, or is

—CH$_2$OH,

—CONH(CH$_2$)$_n$X, or

—COB wherein X is as defined above, B is a protein or lipid residue, n is a number from 1 to 12, or if R$_1$, R$_2$ and R$_3$ are hydrogen atoms, both V's together are the group

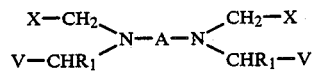

wherein X is as defined above, w is the number 1, 2 or 3, provided that at least two of the substituents Y represent metal ion equivalents of an element with an atomic number of 21 to 29, 42, 44 or 57 to 83.

New such salts include complex salts of the formula

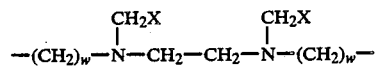

wherein X, A, V and R$_1$ are as defined above provided they contain 3 to 12 substituents Y, of which at least two are a metal ion equivalent of an element with an atomic number of 21 to 29, 42, 44 or 57 to 83 and, in addition, at least one substituent Y is the physiologically biocompatible cation of an organic base or amino acid, wherein the optionally remaining substituents Y represent hydrogen atoms or cations of an inorganic base.

DETAILED DISCUSSION

The element of the above-mentioned atomic number which forms the central ion or ions of the physiologically well tolerated complex salt, obviously must not be radioactive for the intended use of the diagnostic medium according to this invention.

If the medium according to the invention is intended to be used in NMR diagnosis (see, e.g., European patent application No. 71 564 as well as parent Ser. No. 401,594, both of which are entirely incorporated by reference herein), the central ion of the complex salt must be paramagnetic. It preferably is the divalent or trivalent ions of elements with an atomic number of 21 to 29, 42, 44 and 58 to 70. Suitable ions, for example, include chromium(III), manganese(II), iron(III), iron-(II), cobalt(II), nickel(II), copper(II), praseodymium- (III), neodymium(III), samarium(III) and ytterbium-(III). Because of their very strong magnetic moments, gadolinium(III), terbium(III), dysprosium(III), holmium(III), and erbium(III) are preferred.

If the medium according to the invention is intended for use in X-ray diagnosis, the central ion has to be derived from an element with a higher atomic number to achieve a sufficient absorption of X-rays. It has been found that diagnostic media containing a physiologically well tolerated complex salt with central ions of elements with atomic numbers of 57 to 83 are suitable for this purpose. These include, for example, lanthanum(III), the above mentioned ions of the lanthanide group, gold(III), lead(II) or, especially, bismuth(III).

All of the media according to the invention, also intended for use both in NMR and X-ray diagnosis, are also suitable for use in ultrasonic diagnosis.

By "complexing acid" herein is meant an acid which acts as a ligand for the metals of interest thereby forming a chelate therewith.

Suitable complexing acids include those which are customarily used for complexing of the above mentioned central ions. These include, for example, those containing 3 to 12, preferably 3 to 8, methylene phosphonic acid groups, methylene carbohydroxamic acid groups, carboxyethylidene groups, or especially carboxymethylene groups, one, two or three of which are bonded to a nitrogen atom supporting the complexing. If three of the acid groups are bonded to a nitrogen atom, then the underlying acids complexing the complex salts of formula II are present. If only one or two of the acid groups are bonded to a nitrogen atom, that nitrogen is bonded to another nitrogen atom by an optionally substituted ethylene group or by up to four separate ethylene units separated by a nitrogen or oxygen or sulfur atom supporting the complexing. Complexing acids of this type are preferably those of formula I.

The complexing acids can be coupled as conjugates with biomolecules that are known to concentrate in the organ or part of the organ to be examined. These biomolecules include, for example, hormones such as insulin, prostaglandins, steroid hormones, amino sugars, peptides, proteins, lipids etc. Conjugates with albumins, such as human serum albumin, antibodies, for example, monoclonal antibodies specific to tumor associated antigens, or antimyosin etc. are especially notable. The diagnostic media formed therefrom are suitable, for example, for use in tumor and infarct diagnosis. Conjugates with liposomes, or by inclusion of the salts in liposomes, in both cases which, for example, are used as unilamellar or multilamellar phosphatidylcholine-cholesterol vesicles, are suitable for liver examinations. Conjugating can be conventionally effected either via a carboxyl group of the complexing acid or, in the case of proteins or peptides, also by a $(CH_2)_p\text{—}C_6H_4\text{—}W\text{—}$ group, as defined for $R_3$ above. Several acid radicals can be partially bonded to the macromolecular biomolecule in the conjugation of the complex salts with proteins, peptides or lipids. In this case, each complexing acid radical can carry a central ion. If the complexing acids are not bonded to biomolecules, they optionally carry two central ions, usually and especially one central ion.

Suitable complex salts of formula I include, for example, those of formula Ia

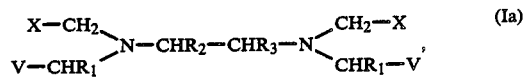

where X, V, $R_1$, $R_2$ and $R_3$ are as defined above.

The following complexing acids, among others, are suitable for production of the complex salts of formula Ia: ethylenediaminetetraacetic acid, ethylenediaminetetraacethydroxamic acid, trans-1,2-cyclohexenediaminetetraacetic acid, dl-2,3-butylenediamine tetraacetic acid, dl-1,2-butylenediaminetetraacetic acid, dl-1,2-diaminepropanetetraacetic acid, 1,2-diphenylethylenediaminetetraacetic acid, ethylenedinitrilotetrakis(methane phosphonic acid) and N-(2-hydroxyethyl)-ethylenediaminetriacetic acid.

Other suitable complex salts of formula I include, for example, those of formula Ib

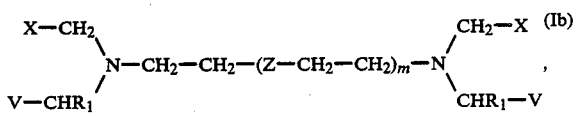

where X, V, Z, $R_1$ and m are as defined above. If Z is an oxygen atom or a sulfur atom, complex salts with m equal to 1 or 2 are preferred.

The following complexing acids, among others, are suitable for production of the complex salts of formula Ib: diethylenetriaminepentaacetic acid, triethylenetetraaminehexaacetic acid, tetraethylenepentaamineheptaacetic acid, 13,23-dioxo-15,18,21-tris(carboxymethyl)-12,15,18,21,24-pentaazapentatriazcontanedioic acid, 3,9-bis-(1-carboxyethyl)-3,6,9-triazaundecanedioic acid, diethylenetriaminepentakis-(methylene phosphonic acid), 1,10-diaza-4,7-dioxadecane-1,1,10,10-tetraacetic acid and, 1,10-diaza-4,7-dithiadecane-1,1,10,10-tetraacetic acid.

Moreover, suitable complex salts of formula I, include those of formula Ic

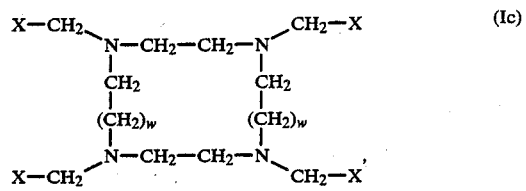

where X and w are as defined above.

The following complexing acids, among others, are suitable for production of the complex salts of formula Ic: 1,4,8,11-tetraazacyclotetradecanetetraacetic acid and especially 1,4,7,10-tetraazacyclododecanetetraacetic acid.

Other complexing acids, which are suitable for production of the complex salts of formula I, include for example: 1,2,3-tris-[bis-(carboxymethyl)-amino-]-propane and nitrilotris-(ethylenenitrilo)-hexaacetic acid. Nitrilotriacetic acid is an example of a complexing acid suitable for production of the complex salts of formula II.

If not all of the hydrogen atoms of the complexing acids are substituted by the central ion or central ions, it is advantageous to increase the solubility of the complex salt to substitute the remaining hydrogen atoms with physiologically biocompatible cations of inorganic and- /or organic bases or amino acids. For example, the lithium ion, the potassium ion and especially the sodium ion are suitable inorganic cations. Suitable cations of organic bases include, among others, those of primary, secondary or tertiary amines, for example, ethanolamine, diethanolamine, morpholine, glucamine, N,N-dimethylglucamine or especially N-methylglucamine. Lysines, arginines or ornithines are suitable cations of amino acids, as generally are those of other basic naturally occurring such acids.

All of the complexing acids used in the agents according to the invention are known or can be produced in a way fully conventional in the art. Thus, for example, production of 13,23-dioxo-15,18,21-tris(carboxymethyl)-12,15,18,21,24-pentaazapentatriacontanedioic acid is produced in an improvement of the method proposed by R. A. Bulman et al. in Naturwissenschaften 68 (1981) 483, as follows:

17.85 g (=50 mmole) of 1,5-bis(2,6-dioxomorpholino)-3-azapentane-3-acetic acid is suspended in 400 ml of dry dimethylformamide and heated for 6 hours to 70° C. after addition of 20.13 g (=100 mmole) of 11-aminoundecanoic acid. The clear solution is concentrated in vacuo. The yellow oil residue is stirred with 500 ml of water at room temperature. In this way, a white, voluminous solid precipitates which is suctioned off and washed several times with water. The resulting product is put into 200 ml of acetone for further purification and stirred for 30 minutes at room temperature. After suctioning off and drying in vacuo at 50° C., 36.9 g (=97% of theory) of a white powder with a melting point of 134°–138° C. is obtained.

Conjugation of the complexing acids with biomolecules also occurs by methods fully conventional in the art, for example, by reaction of nucleophilic groups of biomolecules, for example, amino, hydroxy, thio or imidazole groups with an activated derivative of the complexing acid. For example, acid chlorides, acid anhydrides, activated esters, nitrenes or isothiocyanates can be used as activated derivatives of complexing acids. On the other hand, it is also possible conventionally to react an activated biomolecule with the complexing acid. Substituents of the structure $-C_6H_4N_2+$ or $C_6H_4NHCOCH_2-$ halogen can also be used for conjugating with proteins.

Production of the complex salts is also known or can be performed fully conventionally as known in the art, e.g., in processes in which the metal oxide or a metal salt (for example, nitrate, chloride or sulfate) of an element with an atomic number of 21 to 29, 42, 44 or 57 to 83 is dissolved or suspended in water and/or a lower alcohol (such as methyl, ethyl or isopropyl alcohol) and added to a solution or suspension of the equivalent amount of the complexing acid in water and/or a lower alcohol and stirred, if necessary, with heating moderately or to the boiling point, until the reaction is completed. If the complex salt that is formed is insoluble in the solvent that is used, it is isolated by filtering. If it is soluble, it can be isolated by evaporation of the solvent to dryness, for example, by spray drying.

If acid groups are still present in the resulting complex salt, it is often advantageous to convert the acidic complex salt into a neutral complex salt by reaction with inorganic and/or organic bases or amino acids, which form physiologically biocompatible cations, and isolate them. In many cases, the procedure is even unavoidable since the dissociation of the complex salt is moved toward neutrality to such an extent by a shift in the pH value during the preparation that only in this way is the isolation of homogeneous products or at least their purification made possible. Production is advantageously performed with organic bases or basic amino acids. It can also be advantageous, however, to perform the neutralization by means of inorganic bases (hydroxides, carbonates or bicarbonates) of sodium, potassium or lithium.

To produce the neutral salts, enough of the desired base can be added to the acid complex salts in an aqueous solution or suspension that the point of neutrality is reached. The resulting solution can then be concentrated to dryness in vacuo. It is often advantageous to precipitate the neutral salts by addition of solvents miscible with water, for example, lower alcohols (methyl, ethyl, isopropyl alcohols, etc.), lower ketones (acetone, etc.), polar ethers (tetrahydrofuran, dioxane, 1,2-dimethoxyethane, etc.) and thus obtain crystallizates that isolate easily and purify well. It has been found particularly advantageous to add the desired bases to the reaction mixture even during complexing and thus eliminate a process stage.

If the acid complex salts contain several free acid groups, it is then often advantageous to produce neutral mixed salts which contain both inorganic and organic physiologically biocompatible cations as counterions. This can be done, for example, by reacting the complexing acids in an aqueous suspension or solution with the oxide or salt of the element supplying the central ion and less than the full amount of an organic base necessary for neutralization, e.g., half, isolating the complex salt that is formed, purifying it, if desired, and then adding it to the amount of inorganic base necessary for complete neutralization. The sequence of adding the bases can also be reversed.

Production of the diagnostic media according to the invention is also performed in a way known in the art. For example, the complex salts, optionally with addition of the additives customary in galenicals, are suspended or dissolved in an aqueous medium and then the solution or suspension is sterilized. Suitable additives include, for example, physiologically biocompatible buffers (as, for example, tromethamine hydrochloride), slight additions of complexing agents (as, for example, diethylenetriaminepentaacetic acid) or, if necessary, electrolytes (for example, sodium chloride).

In principle, it is also possible to produce the diagnostic media according to the invention without isolating the complex salts. In this case, special care must be taken to perform the chelating so that the salts and salt solutions according to the invention are essentially free of uncomplexed, toxically active metal ions. This can be assured, for example, using color indicators such as xylenol orange by control titrations during the production process. The invention therefore also relates to the process for production of the complex compound and its salts. A purification of the isolated complex salt can also be employed as a final safety measure.

If suspensions of the complex salts in water or physiological salt solutions are desired for oral administration or other purposes, a small amount of soluble complex salt is mixed with one or more of the inactive ingredients customary in galenicals and/or surfactants and/or aromatics for flavoring.

The diagnostic media according to this invention preferably contain 1 μmole to 1 mole per liter of the complex salt and, as a rule, are administered in doses of 0.001 to 5 mmole/kg. They are intended for oral and particularly parenteral administration.

The media according to the invention, meet the various requirements for suitability as contrast media for nuclear spin tomography. They are exceptionally suitable for improving the image, e.g., its expressiveness, which is obtained with nuclear spin tomography by enhancement of the signal strength after oral or parenteral application. Moreover, they exhibit the great effectiveness that is necessary to load the body with the least possible amount of foreign substances while achieving beneficial results, and the good tolerance that is necessary to maintain the noninvasive character of the examination. (The compounds mentioned, for example in J. Comput. Tomography 5,6:543–46 (1981), in Radiology 144, 343 (1982) and in Brevet Special de Medicament No. 484M (1960) are too toxic). The good aqueous solubility of the media according to the invention makes it possible to produce highly concentrated solutions and in this way to keep the volume load of the circulatory system within supportable limits and compensate for dilution by the body fluids, i.e., NMR diagnostic media must be 100 to 1000 times more soluble in water than for conventional NMR spectroscopy. Moreover, the media according to the invention exhibit not only a great stability in vitro but also an exceptionally great stability in vivo, so that a release or exchange of the ions, which are not covalently bonded in the complexes and which in themselves would be toxic in the 24 hours in which—as pharmacological research has shown—the new contrast media are generally completely eliminated, occurs only extremely slowly. For example, the conjugates with proteins and antibodies used for tumor diagnosis, even in very low dosage, result in such a surprisingly great enhancement of the signal that in this case solutions in correspondingly low concentrations can be applied.

The media according to the invention are also exceptionally suitable as X-ray contrast media. In this case, it should be particularly stressed that with them no indications of anaphylactic type reactions can be detected as opposed to contrast media containing iodine which are known in biochemical and pharmacological tests. These agents of this invention are especially valuable because of the favorable absorption properties in the range of higher X-ray tube voltages for digital subtraction techniques.

The media according to the invention are also suitable as ultrasonic diagnostic media because of their property of favorably influencing the ultrasonic rate.

In contrast to conventional X-ray diagnosis with radiopaque X-ray contrast media, in NMR diagnosis with paramagnetic contrast medium there is no linear dependence of the signal enhancement on the concentration used. As control tests show, an increase in the applied dosage does not necessarily contribute to a signal enhancement, and with a high dosage of paramagnetic contrast medium the signal can even be obliterated. For this reason, it was surprising that some pathological processes can be seen only after application of a strongly paramagnetic contrast medium, according to the invention, higher than the doses indicated in EP No. 71564 (which can be from 0.001 mmole/kg to 5 mmole/kg). Thus, for example, a defective blood-brain barrier in the region of a cranial abscess can be detected only after a dose of 0.05-2.5 mmole/kg, preferably 0.1-0.5 mmole/kg, of paramagnetic complex salts of this invention, for example, gadolinium diethylenetriaminepentaacetic acid or manganese-1,2-cyclohexenediaminetetraacetic acid in the form of their salts that have good aqueous solubility. For a dose greater than 0.1 mmole/kg, solutions of high concentrations up to 1 mole/l, preferably 0.25 to 0.75 mole/l, are necessary, since only in this way is the volume load reduced and handling of the injection solution assured.

Particularly low dosages (under 1 mg/kg) and thus lower concentrated solutions (1 μmole/l to 5 mmole/l), than indicated in EP No. 71564, can be used in this invention for organ-specific NMR diagnosis, for example, for detection of tumors and cardiac infarction.

Generally, the agents of this invention are administered in doses of 0.001-5 mmole/kg, preferably 0.005-0.5 mmole/kg for NMR diagnostics; in doses of 0.1-5 mmole/kg, preferably 0.25-1 mmole/kg for X-ray diagnostics, e.g., analogous to meglumine-diatrizoate, and in doses of 0.1-5 mmole/kg, preferably 0.25-1 mmole/kg for ultrasound diagnostics.

Without further elaboration, it is believed that one skilled in the art can, using the preceding description, utilize the present invention to its fullest extent. The following preferred specific embodiments are, therefore, to be construed as merley illustrative, and not limitative of the remainder of the disclosure in any way whatsoever. In the following examples, all temperatures are set forth uncorrected in degrees Celsius; unless otherwise indicated, all parts and percentages are by weight.

An especially preferred salt of this invention, inter alia, is that of example 5 (Production of the di-N-Methylglucamine salt of gadolinium(III) complex of diethylenetriamine-N,N,N',N'',N''-pentaacetic acid, $C_{28}H_{54}GdN_5O_{20}$).

EXAMPLE 1

Production of the gadolinium(III) complex of nitrilo-N,N,N-triacetic acid $C_6H_6GdNO_6$ The suspension of 36.2 g (=100 mmoles) of gadolinium oxide ($Gd_2O_3$) and 38.2 g (=200 mmoles) of nitrilotriacetic acid in 1.2 liters of water is heated to 90° C. to 100° C. with stirring and is stirred at this temperature for 48 hours. Then the insoluble part is filtered off with activated carbon and the filtrate is evaporated to dryness. The amorphous residue is pulverized.

Yield: 60 g; (87% of theory).

Melting point: 300° C.

The iron(III) complex of nitrilo-N,N,N-triacetic acid is obtained with the aid of iron(III) chloride, $FeCl_3$.

EXAMPLE 2

Production of the disodium salt of gadolinium(III) complex of 13,23-dioxo-15,18,21-tris(carboxymethyl)-12,15,18,21,24-pentaazapentatriacontanedioic acid, $C_{36}H_{60}GdN_5O_{12}\cdot 2Na$ 15.2 g (=20 mmoles) of 13,23-dioxo-15,18,21-tris(carboxymethyl)-12,15,18,21,24-pentaazapentatriacontanedioic acid are suspended in 400 ml of water and heated to 95° C. 7.43 g (=20 mmoles) of gadolinium(III) chloride hexahydrate, dissolved in 60 ml of water, are slowly added drop by drop. It is kept at this temperature for 2 hours and then mixed with 60 ml of 1N sodium hydroxide solution to neutralize the resulting hydrochloric acid.

After complete reaction (tresting with xylenol orange), the resulting precipitation is filtered and washed with water until free of chloride. 17.60 g (96% of theory) of a white powder, insoluble in water, with a melting point of 290°–292° C. are obtained.

Gadolinium(III) complex of 13,23-dioxo-15,18,21-tris(carboxymethyl)-12,15,18,21,24-pentaazapentatriacontanedioic acid.

14.6 g (=16 mmoles) of the gadolinium(III) complex thus obtained are suspended in 200 ml of water and mixed drop by drop with 31.4 ml of 1N sodium hydroxide solution. After 1 hour, a clear solution is obtained, filtered and then concentrated in vacuo. After drying in vacuo at 80° C., 13.2 g (87% of theory) of a white powder, with good aqueous solubility and a melting point of 279°–285° C., are obtained.

Similarly, di-N-methylglucamine salt of gadolinium-(III) complex of 13,23-dioxo-15,18,21-tris(carboxymethyl)-12,15,18,21,24-pentaazapentatriacontanedioic acid, $C_{50}H_{96}GdN_7O_{22}$ is obtained with N-methylglucamine instead of sodium hydroxide solution.

EXAMPLE 3

Production of the disodium salt of gadolinium(III) complex of 3,9-bis(1-carboxyethyl)-6-carboxymethyl-3,6,9-triazaundecanedioic acid, $C_{16}H_{22}GdN_3O_{10}.2Na$ 36.2 g (=0.1 mole) of gadolinium(III) oxide and 84.2 g (=0.2 mole) of 3,9-bis(1-carboxyethyl)-6-carboxymethyl-3,6,9-triazaundecanedioic acid are suspended in 250 ml of water and refluxed for 1 hour. The small amount of insoluble material is filtered off and the solution is concentrated to dryness in vacuo. The residue is pulverized and dried at 60° C. in vacuo. 112.8 g (=98% of theory) of the chelate are obtained as white powder.

57.6 g (=0.1 mole) of the chelate are introduced in a solution of 0.1 mole of sodium hydroxide in 100 ml of water. The solution is set at a pH of 7.5 by addition of another 0.1 mole of sodium hydroxide powder, the solution is heated to boiling and ethyl alcohol is added drop by drop until permanent clouding. After several hours of stirring in an ice bath, the crystallizate is suctioned off, washed with ethyl alcohol and dried in vacuo. The disodium salt is obtained as a white powder in quantitative yield.

EXAMPLE 4

Production of the dimorpholine salt of gadolinium(III) complex of 3,9-bis(1-carboxyethyl)-6-carboxymethyl-3,6,9-triazaundecanedioic acid, $C_{24}H_{42}GdN_5O_{12}$ 17.4 g (=0.2 mole) of morpholine are dissolved in 50 ml of water. 42.1 g (=0.1 mole) of 3,9-bis(1-carboxyethyl)-6-carboxymethyl-3,6,9-triazaundecanedioic acid and then 18.2 g (=0.05 mole) of gadolinium(III) oxide are added and refluxed until a clear solution occurs. Then acetone is added drop by drop by drop until a permanent clouding. After several hours stirring in an ice bath, the crystallizate is suctioned off, washed with acetone and dried in vacuo. Dimorpholine salt is obtained in quantitative amount as a white powder.

EXAMPLE 5

Production of the di-N-Methylglucamine salt of gadolinium(III) complex of diethylenetriamine-N,N,N',N'',N''-pentaacetic acid, $C_{28}H_{54}GdN_5O_{20}$ 39.3 g (=100 mmoles) of diethylenetriamine-N,N,N',N'',N''-pentaacetic acid are suspended in 200 ml of water and mixed with 19.5 g (=100 mmoles) of N-methylglucamine. Then 18.12 g (=50 mmoles) of gadolinium(III) oxide, $Gd_2O_3$ are added in portions and the resulting suspension is heated to 95° C. After about 1 hour, it is mixed with another 19.5 g (=100 mmoles) of N-methylglucamine and, after two more hours of heating, a clear solution is obtained. After complete reaction (testing with xylenol orange) it is filtered from the small amount of undissolved material and the filtrate is concentrated in vacuo to dryness. The residue is again dissolved in 100 ml of water and stirred into 250 ml of ethyl alcohol. After several hours of cooling, the crystallizate is suctioned off, washed with cold ethly alcohol and dried at 60° in vacuo. 92.7 g (99% of theory) of a white powder with an uncharacteristic melting point is obtained.

Acetone, propyl alcohol or isopropyl alcohol can also be used instead of ethyl alcohol for purifying the complex salt.

Correspondingly, there are obtained:

with dysprosium(III) oxide, $Dy_2O_3$
di-N-methylglucamine salt of dysprosium(III) complex of diethylenetriamine-N,N,N',N'',N''-pentaacetic acid, $C_{28}H_{54}DyN_5O_{20}$;

with lanthanum(III) oxide, $La_2O_3$
di-N-methylglucamine salt of lanthanum(III) complex of diethylenetriamine-N,N,N',N'',N''-pentaacetic acid, $C_{28}H_{54}LaN_5O_{20}$;

with ytterbium(III) oxide, $Yb_2O_3$
di-N-methylglucamain salt of ytterbium(III) complex of diethylenetriamine-N,N,N',N'',N''-pentaacetic acid, $C_{28}H_{54}YbN_5O_{20}$ with samarium(III) oxide, $Sm_2O_3$
di-N-methylglucamine salt of samarium(III) complex of diethylenetriamine-N,N,N',N'',N''-pentaacetic acid, $C_{28}H_{54}SmN_5O_{20}$;

with holmium(III) oxide, $Ho_2O_3$
di-N-methylglucamine salt of holmium(III) complex of diethylenetriamine-N,N,N',N'',N''-pentaacetic acid, $C_{28}H_{54}HoN_5O_{20}$;

with bismuth(III) oxide, $Bi_2O_3$
di-N-methylglucamine salt of bismuth(III) complex of diethylenetriamine-N,N,N',N'',N''-pentaacetic acid, $C_{28}H_{54}BiN_5O_{20}$;

with gadolinium(III) oxide, $Gd_2O_3$
tri-N-methylglucamine salt of gadolinium(III) complex of triethylenetetraamine-N,N,N',N'',N''',N'''-hexaacetic acid, $C_{39}H_{78}GdN_7O_{27}$;

Further, there are obtained:

with holmium(III) oxide, $Ho_2O_3$ and ethanolamine instead of N-methylglucamine
diethanolamine salt of holmium(III) complex of diethylenetriamine-1N,N,N',N'',N''-pentaacetic acid, $C_{18}H_{34}HoN_5O_{12}$;

with gadolinium(III) oxide, $Gd_2O_3$ and lysine instead of N-methylglucamine
dilysine salt of gadolinium(III) complex of diethylenetriamine-N,N,N',N'',N''-pentaacetic acid, $C_{26}H_{48}GdN_7O_{14}$.

With the use of diethanolamine
the di-diethanolamine salt of holmium(III) complex of diethylenetriaminepentaacetic acid, $C_{22}H_{42}HoN_5O_{14}$.

The salts appear as white powders with an uncharacteristic melting point.

EXAMPLE 6

Production of the disodium salt of gadolinium(III) complex of diethylenetriamine-N,N,N',N'',N''-pentaacetic acid, $C_{14}H_{18}GdN_3O_{10}\cdot 2Na$ 18.2 g (=0.05 mole) of gadolinium(III) oxide and 39.3 g (=0.1 mole) of diethylenetriaminepentaacetic acid are suspended in 110 ml of water and refluxed for 1 hour. The clear solution is cooled and brought to pH 7.5 by addition of about 80 ml of 5N sodium hydroxide solution. It is again heated to boiling and 250 ml of ethyl alcohol are added drop by drop. After several hours of stirring in an ice bath, the crystallizate is suctioned off, washed with ice-cold ethyl alcohol and dried in vacuo at 60° C. A white powder, that does not melt up to 300° C., is obtained in quantitative amount.

In a corresponding way, there are obtained:
with dyprosium(III) oxide, $Dy_2O_3$
disodium salt of dyprosium(III) complex of diethylenetriamine-N,N,N',N'',N''-pentaacetic acid, $C_{14}H_{18}LaN_3O_{10}\cdot 2Na$;
with lanthanum(III) oxide, $La_2O_3$
disodium salt of lanthanum(III) complex of diethylenetriamine-N,N,N',N'',N''-pentaacetic acid, $C_{14}H_{18}LaN_3O_{10}\cdot 2Na$;
with holmium(III) oxide, $Ho_2O_3$
disodium salt of holmium(III) complex of diethylenetriamine-N,N,N',N'',N''-pentaacetic acid, $C_{14}H_{18}HoN_3O_{10}\cdot 2Na$;
with ytterbium(III) oxide, $Yb_2O_3$
disodium salt of ytterbium(III) complex of diethylenetriamine-N,N,N',N'',N''-pentaacetic acid, $C_{14}H_{18}YbN_3O_{10}\cdot 2Na$;
with samarium(III) oxide, $Sm_2O_3$
disodium salt of samarium(III) complex of diethylenetriamine-N,N,N',N'',N''-pentaacetic acid, $C_{14}H_{18}SmN_3O_{10}\cdot 2Na$;
with erbium(III) oxide, $Eb_2O_3$
disodium salt of erbium(III) complex of diethylenetriamine-N,N,N',N'',N''-pentaacetic acid, $C_{14}H_{18}EbN_3O_{10}\cdot 2Na$;
with gadolinium(III) oxide, $Gd_2O_3$
sodium salt of digadolinium(III) complex of tetraethylenepentamine-N,N,N',N'',N''',N'',N''-heptaacetic acid, $C_{22}H_{30}Gd_2N_5O_{14}\cdot Na$.

These salts appear as white powders with an uncharacteristic melting point and have a very good aqueous solubility.

EXAMPLE 7

Production of the N-methylglucamine salt of iron(III) complex of diethylenetriaminepentaacetic acid, $C_{21}H_{37}FeN_4O_{15}$ 35.40 g (=90 mmoles) of diethylenetriaminepentaacetic acid are suspended in 100 ml of water and mixed with 24.3 g (=90 mmoles) of iron(III) chloride hexahydrate ($FeCl_3\cdot 6H_2O$) dissolved in 100 ml of water. The suspension, which is dark brown at first, is heated to 95° C. After about 1 hour, the color changes to light yellow. 270 ml of 1N sodium hydroxide solution is added to neutralize the resulting hydrochloric acid and it is heated for another 3 hours to 95° C. The resulting light yellow precipitate is suctioned off, washed with water until free of chloride and dried in vacuo at 60° C. 17.85 g (45% of theory) of a light yellow powder, with a melting point of >300° C., is obtained.

17.85 g (=40 mmoles) of the resulting iron(III) complex are suspended in 200 ml of water and thoroughly mixed in portions with 7.8 g (=40 mmoles) of N-methylglucamine. It is heated for about 3 hours to 50° C. and a nearly clear, reddish brown solution is obtained, which is filtered and then concentrated in vacuo to dryness. The residue is dried in vacuo at 50° C. 24.3 g (95% of theory) of a reddish brown powder with a melting point of 131°-133° C. are obtained.

With sodium hydroxide solution instead of the organic bases, there are obtained:
sodium salt of iron(III) complex of ethylenediaminetetraacetic acid, $C_{10}H_{12}FeN_2O_8\cdot Na$
sodium salt of iron(III) complex of trans-1,2-cyclohexenediaminetetraacetic acid, $C_{14}H_{18}FeN_2O_8\cdot Na$
disodium of iron(III) complex of diethylenetrinitrilopenta(methanephosphonic acid), $C_9H_{23}FeN_3O_{15}P_5\cdot 2Na$
sodium salt of iron(III) complex of 1,10-diaza-4,7-dioxadecane-1,1,10,10-tetraacetic acid, $C_{14}H_{20}FeN_2O_{10}\cdot Na$
sodium salt of iron(III) complex of ethylenediaminetetraacethydroxamic acid, $C_{10}H_{16}FeN_6O_8\cdot Na$.

In a corresponding way, there are obtained with N-methylglucamine:
di-N-methylglucamine salt of iron(III) complex of diethylenetriamine-N,N,N',N'',N''-pentaacetic acid, $C_{28}H_{54}FeN_5O_{20}$
N-methylglucamine salt of iron(III) complex of trans-1,2-cyclohexenediamine-N,N,N',N'-tetraacetic acid, $C_{21}H_{36}FeN_3O_{13}$
N-methyleglucamine salt of iron(III) complex of ethylenediamine-N,N,N',N'-tetraacetic acid, $C_{17}H_{30}FeN_3O_{13}$
tri-N-methylglucamine salt of iron(III) complex of triethylenetriamine-N,N,N',N'',N''',N'''-hexaacetic acid, $C_{39}H_{78}FeN_7O_{27}$.

With the use of diethanolamine instead of N-methylglucamine, di-diethanolamine salt of iron(III) complex of diethylenetriamine-N,N,N',N'',N''-pentaacetic acid, $C_{22}H_{42}FeN_5O_{14}$ is obtained.

EXAMPLE 8

Production of the N-methylglucamine salt of gadolinium(III) complex of trans-1,2-cyclohexendiamine-N,N,N',N'-tetraaetic acid, $C_{21}H_{36}GdN_3O_{13}$ 20.78 g (=60 mmoles) of trans-1,2-cyclohexenediamine-N,N,N',N'-tetraacetic acid are suspended in 150 ml of water. After addition of 11.7 g (=60 mmoles) of N-methylglucamine, a nearly clear solution is obtained, to which 10.88 g (=30 mmoles) of gadolinium oxide ($Gd_2O_3$) are added. The newly resulting suspension is heated for 6 hours to 95° C. It is filtered off from the small amount of undissolved material and the filtrate concentrated to dryness. The residue is dried in vacuo at 60° C. and pulverized. 38.6 g (92% of theory) of a white powder with a melting point of 258°-261° C. are obtained.

In a similar way, the sodium salt of gadolinium(III) complex of trans-1,2-cyclohexenediamine-N,N,N',N'-tetraacetic acid, $C_{14}H_{18}GdN_2O_8\cdot Na$ is obtained with sodium hydroxide solution instead of N-methylglucamine.

The sodium salt of chromium(III) complex of ethylenediamine-N,N,N',N'-tetraacetic acid, $C_{10}H_{12}CrN_2O_8 \cdot Na$ is obtained with freshly precipitated chromium(III) hydroxide, $Cr(OH)_3$.

EXAMPLE 9

Production of the disodium salt of manganese(II) complex of trans-1,2-cyclohexylenediamine-N,N,N',N'-tetraacetic acid, $C_{14}H_{18}MnN_2O_8 \cdot 2Na$ 34.6 g (=100 mmoles) of trans-1,2-cyclohexenediamine-N,N,N',N'-tetraacetic acid are suspended under nitrogen in 100 ml of water and mixed with 11.5 g (=100 mmoles) of manganeses(II) carbonate, $MnCO_3$. It is heated to 95° C. and 200 ml of 1N sodium hydroxide solution are added drop by drop. The clear solution is concentrated in vacuo and the residue dried in vacuo at 60° C. 40.8 g (92% of theory) of a pink powder are obtained.

In a corresponding way there are obtained:
from copper(II) carbonate the disodium salt of copper(II) complex of trans-1,2-cyclohexenediaminetetraacetic acid, $C_{14}H_{18}CuN_2O_8 \cdot 2Na$;
from cobalt(II) carbonate the disodium salt of cobalt(II) complex of trans-1,2-cyclohexenediaminetetraacetic acid, $C_{14}H_{18}CoN_2O_8 \cdot 2Na$;
from nickel(II) carbonate the disodium salt of nickel(II) complex of trans-1,2-cyclohexenediaminetetraacetic acid, $C_{14}H_{18}NiN_2O_8 \cdot 2Na$.

With N-methylglucamine instead of sodium hydroxide solution, the following are obtained:
di-N-methylglucamine salt of manganese(II) complex of trans-1,2-cyclohexenediaminetetraacetic acid, $C_{28}H_{52}MnN_4O_{18}$;
di-N-methylglucamine salt of manganese(II) complex of dl-2,3-butylenediaminetetraacetic acid, $C_{26}H_{52}MnN_4O_{18}$;
di-N-methylglucamine salt of manganese(II) complex of ethylenediamine-N,N,N',N'-tetraacetic acid, $C_{24}H_{48}MnN_4O_{18}$;
di-N-methylglucamine salt of manganese(II) complex of dl-1,2-butylenediamine-N,N,N',N'-tetraacetic acid, $C_{26}H_{52}MnN_4O_{18}$;
di-N-methylglucamine salt of manganese(II) complex of dl-1,2-diaminopropane-N,N,N',N'-tetraacetic acid, $C_{25}H_{50}MnN_4O_{18}$;
tri-N-methylglucamine salt of manganese(II) complex of diethylenetriaminepentaacetic acid, $C_{35}H_{72}MnN_6O_{25}$;
with nickel(II) carbonate, $NiCO_3$
di-N-methlglucamine salt of nickel(II) complex of ethylenediamine-N,N,N',N'-tetraacetic acid, $C_{24}H_{48}NiN_4O_{18}$;
with cobalt(II) carbonate, $CoCO_3$ and ethanolamine
diethanolamine salt of cobalt(II) complex of ethylenediamine-N,N,N',N'-tetraacetic acid, $C_{14}H_{28}CoN_4O_{10}$;
with copper(II) carbonate, $CuCO_3$, and ethanolamine
diethanolamine salt of copper(II) complex of ethylenediamine-N,N,N',N'-tetraacetic acid, $C_{14}H_{28}CuN_4O_{10}$;
with manganese(II) carbonate, $MnCO_3$, and diethanolamine
tridiethanolamine salt of manganese(II) complex of diethylenetriamine-N,N,N',N'',N''-pentaacetic acid, $C_{26}H_{54}MnN_6O_{16}$;
with manganese(II) carbonate, $MnCO_3$, and morpholine
dimorpholine salt of manganese(II) complex of ethylenediamine-N,N,N'',N''-tetraacetic acid, $C_{18}H_{32}MnN_4O_{10}$.

EXAMPLE 10

N-methylglucamine salt of gadolinium(III) complex of ethylenediamine-N,N,N',N'-tetraacetic acid, $C_{17}H_{30}GdN_3O_{13}$ 29.2 g (=100 moles) of ethylenediamine-N,N,N',N'-tetraacetic acid are suspended in 100 ml of water and heated to 95° C. with 18.1 g (=50 mmoles) of gadolinium(III) oxide. During heating up, 19.5 g (=100 mmoles) of N-methylglucamine are added by portions. After about 3 hours, a clear solution is obtained, which is filtered and concentrated in vacuo to dryness. The residue is dried in vacuo at 60° C. 61.3 g (95% of theory) of a white powder with an uncharacteristic melting point are obtained.

In an analogous way, there are obtained:
with dysprosium(III) oxide, $Dy_2O_3$
N-methylglucamine salt of dysprosium(III) comples of ethylenediamine-N,N,N',N'-tetraacetic, $C_{17}H_{30}DyN_3O_{13}$;
N-methylglucamine salt of gadolinium(III) complex of 1,10-diaza-4,7-dioxadecane-1,1,10,10-tetraacetic acid, $C_{21}H_{38}GdN_3O_{15}$;
N-methylglucamine salt of gadolinium(III) complex of 1,2-diphenylethylenediaminetetraacetic acid, $C_{29}H_{38}N_3O_{13}Gd$;
with lead(II) oxide, PbO, and sodium hydrochloride
disodium salt of lead(II) complex of ethylenediaminetetraacetic acid, $C_{10}H_{12}N_2O_8Pb \cdot 2Na$;
with freshly precipitated chromium(III) hydroxide, $Cr(OH)_3 \cdot Na$
sodium salt of chromium(III) complex of ethylenediaminetetraacetic acid, $C_{10}H_{12}CrN_2O_8$; and analogously
sodium salt of gadolinium(III) complex of ethylenediaminetetraacethydroxiamic acid, $C_{10}H_{16}GdN_6O_8 \cdot Na$;
sodium salt of gadolinium(III) complex of ethylenediamine-N,N,N',N'-tetraacetic acid, $C_{10}H_{12}GdN_2O_8 \cdot Na$.

EXAMPLE 11

Production of the sodium salt of gadolinium(III) complex of 1,4,7,10-tetraazacyclododecane-N,N',N'',N'''-tetraacetic acid, $C_{16}H_{24}GdN_4O_8 \cdot Na$ 4.0 g (=10 mmoles) of 1,4,7,10-tetraazacyclododecane-N,N',N'',N'''-tetraacetic acid are suspended in 20 ml of water and mixed with 10 ml of 1N sodium hydroxide solution. 1.8 g (=5 mmoles) of gadolinium(III) oxide, $Gd_2O_3$, are added and the suspension is heated for 2 hours to 50° C. The clear solution is filtered and concentrated in vacuo. The residue is dried and pulverized. 5.5 g (95% of theory) of a white powder are obtained.

In a similar way, there are obtained:
N-methylglucamine salt of gadolinium(III) complex of 1,4,7,10-tetraazacyclododecane-N,N',N'',N'''-tetraacetic acid, $C_{23}H_{42}GdN_5O_{13}$
sodium salt of gadolinium(III) complex of 1,4,8,11-tetraazacyclotetradecane-N,N',N',N',N''-tetraacetic acid, $C_{18}H_{28}GdN_4O_8 \cdot Na$.

EXAMPLE 12

Production of the tetra-N-methylglucamine salt of gadolinium(III) complex of ethylenedinitrilo-tetrakis(methanephosphonic acid), $C_{34}H_{85}GdN_6O_{32}P_4$ 9.11 g (=20 mmoles) of ethylenedinitrilo-tetrakis(methanephosphonic acid) are suspended in 150 ml of water and adjusted to a pH of 5 with a suitable amount of N-methylglucamine. 3.6 g (=10 mmoles) of gadolinium(III) oxide, $Gd_2O_3$, are added and heated to 70° C. After about 1 hour a clear solution is obtained, which is mixed with the remaining portion of N-methylglucamine. Altogether, 15.6 g (=80 mmoles) of N-methylglucamine are used. The solution is concentrated in vacuo to dryness and the remaining gelatinous residue is added to 200 ml of acetonitrile. It is stirred at 30° C. for about 20 hours and the resulting fine precipitate is suctioned off. After drying in vacuo at 40° C., 23.4 g (85% of theory) of a white powder with a melting point of 115°–118° C. are obtained.

In a similar way, there are obtained:
hepta-N-methylglucamine salt of gadolinium(III) complex of diethylenetriamine-N,N,N',N'',N''-penta(methanephosphonic acid), $C_{58}H_{144}GdN_{10}O_{50}P_5$
and with the use of sodium hydroxide solution instead of N-methylglucamine
disodium salt of gadolinium(III) complex of diethylenetrinitrilopenta(methanephosphonic acid), $C_9H_{23}GdN_3O_{15}P_5.2Na$

EXAMPLE 13

Production of the disodium salt of manganese(II) complex of ethylenedinitrilotetra(acethydroxamic acid), $C_{10}H_{16}MnN_6O_8.2Na$ 2.30 g of manganese(II) carbonate and 7.05 g of ethylenedinitrilotetra(acethydroxamic acid) are refluxed in 18 ml of water for 3 hours. Then the pH is adjusted to 7 by addition of dilute sodium hydroxide solution and 40 ml of acetone are added drop by drop. After several hours of stirring in an ice bath, the precipitated crystallizate is suctioned off, washed with acetone and dried at 50° C. in vacuo. A dihydrate is obtained in quantitative amount as a white powder with a melting point above 300° C.

EXAMPLE 14

Production of a mixed salt solution of sodium and N-methylglucamine salt of gadolinium(III) complex of diethylenetriaminepentaacetic acid (a) Production of the mono-N-methylglucamine salt of the complex, $C_{21}H_{37}GdN_4O_{15}$ 195.2 g (1 mole) of N-methylglucamine are dissolved in 7 liters of water. Then 393.3 g (1 mole) of diethylenetriaminepentaacetic acid and 181.3 g (0.5 mole) of gadolinium oxide, $Gd_2O_3$, are added and refluxed for 2 hours. The filtered clear solution is spray dried. A white crystalline powder with a water content of 2.6%, which sinters at 133° C. and melts with foaming at 190° C. is obtained.

(b) Production of the neutral mixed salt solution 730.8 g (=1 mole) of the salt obtained under a) are suspended in 630 ml of water p.i. (pro injectione, i.e., sterile) and 40 g (=1 mole) of sodium hydroxide powder are added in portions. Water p.i. is added to the neutral solution to make 100 ml, it is put into bottles through a pyrogen filter and sterilized by heat. This one molar solution contains 753.8 g of mixed salt per liter.

EXAMPLE 15

Production of a solution of the di-N-methylglucamine salt of gadolinium(III) complex of diethylenetriaminepentaacetic acid 535.0 g (=730 mmoles) of the salt described in example 5 are made into a paste in 500 ml of water p.i. and brought to solution by addition of 142.4 g (=730 mmoles) of N-methylglucamine at pH 7.2. Then water p.i. is added to make 1000 ml, the solution is put into ampoules and sterilized by heating.

EXAMPLE 16

Production of a solution of the disodium salt of gadolinium(III) complex of diethylenetriaminepentaacetic acid 485.1 g (=820 mmoles) of the disodium salt obtained in example 6 are made into a paste in 500 ml of water p.i. Then water p.i. is added to make 1000 ml, the solution is put into ampoules and sterilized by heating.

EXAMPLE 17

Production of a solution of the disodium salt of gadolinium(III) complex of 13,23-dioxo-15,18,21-tris(carboxymethyl)-12,15,18,21,24-pentazapentatriacontanedioic acid 392.0 g (=400 mmoles) of the salt described in example 2 are made into a paste in 500 ml of water p.i. and dissolved by adding water p.i. to make 1000 ml with gentle heating. The solution is put into bottles and sterilized by heating.

EXAMPLE 18

Production of a solution of the N-methylglucamine salt of gadolinium(III) complex of 1,4,7,10-tetraazacyclododecanetetraacetic acid 370.9 g (=500 mmoles) of the salt mentioned in example 11 is made into a paste in 500 ml of water p.i. and dissolved by adding water p.i. to make 1000 ml. The solution is put into ampoules and sterilized by heating.

EXAMPLE 19

Production of a solution of the di-N-methylglucamine salt of manganese(II) complex of trans-1,2-cyclohexenediaminetetraacetic acid.

395.9 g (=500 mmoles) of the salt mentioned in example 9 are suspended in 500 ml of water p.i. It is mixed with 1.3 g of ascorbic acid and brought to solution by adding water p.i. to make 1000 ml. The solution is sterilized by filtration and put into ampoules.

EXAMPLE 20

Production of a solution of the tri-N-methylglucamine salt of manganese(II) complex of diethylenetriaminepentaacetic acid 514.4 g (=500 mmoles) fo the salt mentioned in example 9 are suspended in 600 ml of water p.i. It is mixed with 1.3 g of ascorbic acid and dissolved by adding water p.i. to make 1000 ml. The solution is sterilized by filtering and put into ampoules.

EXAMPLE 21

Production of a solution of the di-N-methylglucamine salt of iron(III) complex of diethylenetriaminepentaacetic acid 44.6 g (=0.1 mole) of the iron(III) complex of diethylenetriaminepentaacetic acid obtained in example 7 are suspended in 40 ml of water p.i. After addition of 0.18 g of tromethamine hydrochloride and 39.1 g (=0.2 moles) of N-methylglucamaine it is dissolved to neutrality, water p.i. is added to the solution to bring it to 100 ml, it is put into ampoules and sterilized by heating.

EXAMPLE 22

Production of a solution of the gadolinium(III) complex of nitrilotriacetic acid 1.9 g (=10 mmoles) of nitrilotriacetic acid and 1.8 g (=5 mmoles) of gadolinium(III) oxide are dissolved in 100 ml of water p.i. with heating. The solution is put into ampoules and sterilized by heating.

EXAMPLE 23

Production of a solution of the N-methylglucamine salt of gadolinium(III) complex of ethylenediaminetetraacetic acid.

38.52 g (=60 mmoles) of the substance described in example 10 are dissolved in 70 ml of water p.i. After addition of 0.12 g of water p.i. is added to make 100 ml, the solution is put into ampoules and sterilized by heating.

EXAMPLE 24

Production of a solution of the di-N-methylglucamine salt of dysprosium(III) complex of diethylenetriaminepentaacetic acid 35.7 g (=60 mmoles) of the dysprosium(III) complex of diethylenetriaminepentaacetic acid (8.0% water content) are suspended in 70 ml of water p.i. and brought to solution by addition of 21.2 g (=120 mmoles) of N-methylglucamaine at a pH of 7.5. Then water p.i. is added to make 100 ml, the solution is put into ampoules and sterilized by heating.

EXAMPLE 25

Production of a solution of the N-methylglucamine salt of gadolinium(III) complex of trans-1,2-cyclohexenediaminetetraacetic acid 555.8 g (=0.8 mole) of the salt described in example 8 are dissolved in water p.i. to make 1000 ml. After filtration through a pyrogen filter, the solution is put into ampoules and sterilized by heating.

EXAMPLE 26

Production of a solution of the N-methylglucamine salt of ruthenium(III) complex of 1,10-diaza-4,7-dithiadecane-1,1,10,10-tetraacetic acid 15.6 g (=0.03 mole) of the ruthenium(III) complex of 1,10-diaza-4,7-dithiadecane-1,1,10,10-tetraacetic acid are suspended in 50 ml of water p.i. and brought to solution at pH 7.5 by addition of 5.9 g (=0.03 moles) of N-methylglucamine. Water p.i. is added to make 1000 ml, the solution is put into ampoules and sterilized by heating.

EXAMPLE 27

Production of a solution of the dilysine salt of gadolinium(III) complex of diethylenetriaminepentaacetic acid 273.8 g (=0.5 mole) of the gadolinium(III) complex of diethylenetriaminepentaacetic acid are suspended in 500 ml of water p.i. 292.4 g (=1 mole) of lysine are added, left to stir for several hours with gentle heating and then water p.i. is added to make 1000 ml. The solution is put in bottles and sterilized by heating.

EXAMPLE 28

Production of a solution of the tri-N-methylglucamine salt of molybdenum (VI) complex of diethyelenetriaminepentaacetic acid 18.8 g (=0.28 mole) of the complex $H_3[Mo_2O_2(OH)_4 \cdot C_{14}H_{23}N_3O_{120}]$ are suspended in 50 ml of water p.i. and dissolved to neutrality by addition of 16.4 g (=0.84 mole) of N-methylglucamine. 0.15 g of tromethamine is added, water p.i. is added to make 100 ml, the solution is subjected to sterilization by filtering and put into ampoules.

EXAMPLE 29

Production of a solution of the disodium salt of manganese(II) complex of ethylenediaminetetraacetic acid 343.2 g (=1 mole) of the manganese(II) complex of ethylenediaminetetraacetic acid are suspended in 500 ml of water p.i. and dissolved to neutrality by addition by portions of 80 g (=2 moles) of sodium hydroxide. After addition of 1.5 g of tromethamine, water p.i. is added to the solution to make 1000 ml, it is put into bottles and sterilized by heating.

EXAMPLE 30

Production of a solution of the sodium salt of iron(III) complex of ethylenediaminetetraacetic acid 345.7 g (=1 mole) of the iron(III) complex of ethylenediaminetetraacetic acid are suspended in 500 ml of water p.i. and dissolved to neutrality by addition by portions of 40 g (=1 mole) of sodium hydroxide. After addition of 1.5 g of tromethamine, water p.i. is added to the solution to make 1000 ml, it is put in bottles and sterilized by heating.

EXAMPLE 31

Production of a solution of the disodium salt of iron(III) complex of diethylenetriaminepentaacetic acid 334.6 g (=0.75 mole) of the iron(III) complex of diethylenetriaminepentaacetic acid are suspended in 500 ml of water p.i. and dissolved to neutrality by addition by portions of 60 g (=1.5 moles) of sodium hydroxide. Water p.i. is added to the solution to make 1000 ml, it is put into bottles and sterilized by heating.

EXAMPLE 32

Production of a solution of the sodium salt of gadolinium(III) complex of trans-1,2-cyclohexenediaminetetraacetic acid 558.6 (=1 mole) of the salt mentioned in example 8 are dissolved in water p.i. to 1000 ml. The solution is put into bottles and sterilized by heating.

EXAMPLE 33

Production of a solution of the N-methylglucamaine salt of gadolinium(III) complex of 1,2-diphenylethylenediaminetetraacetic acid 396.9 g (=500 mmoles) of the salt described in example 10 are made into a paste in 600 ml of water p.i. and dissolved by addition of water to make 1000 ml. The solution is put into ampoules and sterilized by heating.

EXAMPLE 34

Production of a solution of the sodium salt of iron(III) complex of ethylenediaminetetraacetic acid 183.5 g (=500 mmoles) of the salt mentioned in example 7 are made into a paste in 500 ml of water p.i. 1.0 g of tromethamine is added, water p.i. is added to make 1000 ml, the solution is put into ampoules and sterilized by heating.

EXAMPLE 35

Production of a solution of the di-N-methylglucamine salt of lanthanum(III) complex of diethylenetriaminepentaacetic acid 459.8 g (=500 mmoles) of the salt mentioned in example 5 are made into a paste in 650 ml of water p.i. and brought to solution by addition of water p.i. to make 1000 ml. The solution is put into ampoules and sterilized by heating.

EXAMPLE 36

Production of a solution of the di-N-methylglucamine salt of bismuth(III) complex of diethylenetriaminepentaacetic acid 692.8 g (=700 mmoles) of the salt mentioned in example 5 are made into a paste in 600 ml of water p.i. and after addition of 1.8 g of tromethamine dissolved by addition of water p.i. to make 1000 ml with gentle heating. The solution is put into ampoules and sterilized by heating.

EXAMPLE 37

Production of a solution of the di-N-methylglucamine salt of holmium(III) complex of diethylenetriaminepentaacetic acid 662.0 g (=700 mmoles) of the salt mentioned in example 5 are made into a paste in 600 ml of water p.i. and after addition of 1.8 g of tromethamine, are dissolved by addition of water p.i. to make 1000 ml with gentle heating. The solution is put into ampoules and sterilized by heating.

EXAMPLE 38

Production of a solution of the di-N-methylglucamine salt of ytterbium(III) complex of diethylenetriaminepentaacetic acid 476.9 g (=500 mmoles) of the salt mentioned in example 5 are made into a paste in 650 ml of water p.i. and after addition of 1.5 g of tromethamine dissolved by addition of water p.i. to make 1000 ml. The solution is put into ampoules and sterilized by heating.

EXAMPLE 39

Production of a solution of the disodium salt of lanthanum(III) complex of diethylenetriaminepentaacetic acid 573.2 g (=1000 mmoles) of the salt mentioned in example 6 are made into a paste in 650 ml of water p.i. and dissolved by addition of water p.i. to make 1000 ml. The solution is put into ampoules and sterilized by heating.

EXAMPLE 40

Production of a solution of the disodium salt of dysprosium(III) complex of diethylenetriaminepentaacetic acid.

477.4 g (=800 mmoles) of the salt mentioned in example 6 are made into a paste in 600 ml of water p.i. and dissolved by addition of water p.i. to make 1000 ml. The solution is put into ampoules and sterilized by heating.

EXAMPLE 41

Production of a solution of the disodium salt of holmium(III) complex of diethylenetriaminepentaacetic acid 299.6 g (=500 mmoles) of the salt mentioned in example 6 are made into a paste in 500 ml of water p.i. and dissolved by addition of water p.i. to make 1000 ml. The solution is put into ampoules and sterilized by heating.

EXAMPLE 42

Production of a solution of the disodium salt of ytterbium(III) complex of diethylenetriaminepentaacetic acid.

303.5 g (=500 mmoles) of the salt mentioned in example 6 are made into a paste in 500 ml of water p.i. and dissolved by addition of water p.i. to make 1000 ml. The solution is put into ampoules and sterilized by heating.

EXAMPLE 43

Production of a solution of the tetra-N-methylglucamine salt of gadolinium(III) complex of ethylenedinitrilo-tetrakis(methanephosphonic acid)

137.1 g (=100 mmoles) of the salt mentioned in example 12 are made into a paste in 500 ml of water p.i. and after addition of 0.8 g of tromethamine are dissolved by addition of water p.i. to make 1000 ml. The solution is put into ampoules and sterilized by heating.

EXAMPLE 44

Production of a solution of gadolinium(III) complex of N'-(2-hydroxyethyl)ethylenediamine-N,N,N'-triacetic acid 1.9 g (=6.7 mmoles) of N'-(2-hydroxyethyl)ethylenediamine-N,N,N'-triacetic acid and 1.2 g (=3.35 moles) of gadolinium(III) oxide are dissolved in 6 ml of water p.i. with heating. The solution is put into ampoules and sterilized by heating.

EXAMPLE 45

Production of a solution of the disodium salt of manganese(II) complex of trans-1,2-cyclohexenediaminetetraacetic acid 44.3 g (=100 mmoles) of the salt mentioned in example 9 are made into a paste under nitrogen cover in 60 ml of water p.i. and brought to solution by addition of water p.i. to make 100 ml. The solution is put into ampoules and sterilized by heating.

EXAMPLE 46

Production of a solution of the sodium salt of gadolinium(III) complex of 1,4,8,11-tetraazacyclotetradecane-N,N',N'',N'''-tetraacetic acid 552.6 g (=1 mole) of the salt mentioned in example 11 are dissolved in water p.i. to make 1000 ml. The solution is put into bottles and sterilized by heating.

EXAMPLE 47

Production of a solution of the disodium salt of bismuth(III) complex of diethylenetriaminepentaacetic acid.

23.4 g (=50 mmoles) of bismuth(III) oxide are suspended in 50 ml of water p.i. After addition of 39.3 g (=100 mmoles) of diethylenetriaminepentaacetic acid and 4.0 g (=50 mmoles) of sodium hydroxide, it is refluxed to a clear solution. The solution, cooled to room temperature, is neutralized by addition of 4.0 g of sodium hydroxide and water p.i. is added to make 100 ml. The solution is put into ampoules and sterilized by heating.

EXAMPLE 48

Production of a solution of the disodium salt of samarium(III) complex of diethylenetriaminepentaacetic acid 58.5 g (=100 mmoles) of the salt mentioned in example 6 are dissolved in 65 ml of water p.i. with heating. Water p.i. is added to make a total volume of 100 ml, it is put into ampoules and sterilized by heating.

EXAMPLE 49

Production of a solution of the di-N-methylglucamine salt of gadolinium(III) complex of 13,23-dioxo-15,18,21-tris(carboxymethyl)-12,15,18,21,24-pentaazapentatriacontanedioic acid 130.4 g (=100 mmoles) of the salt mentioned in example 2 are made into a paste in 250 ml of water p.i. and dissolved with heating. Water p.i. is added to make 500 ml, the solution is put into ampoules and sterilized by heating.

EXAMPLE 50

Production of a solution of the di-N-methylglucamine salt of manganese(II) complex of ethylenediaminetetraacetic acid 3.68 g (=5 mmoles) of the substance described in example 9 are dissolved in 70 ml of water p.i. and the solution is mixed with 0.4 g of sodium chloride. Then water p.i. is added to make 100 ml and the solution is put into ampoules through a sterilizing filter. The solution is isotonic with the blood with 280 mOsm.

EXAMPLE 51

Production of a solution of the disodium salt of gadolinium(III) complex of diethylenetrinitrilopenta(methanephosphonic acid)

38.57 g (=50 mmoles) of the substance described in example 12 are made into a paste in 50 ml of water p.i. The pH is adjusted to 7.2 by addition of sodium hydroxide powder, and water p.i. is added to make 100 ml. The solution is put into ampoules and sterilized by heating.

EXAMPLE 52

Production of a solution of the trisodium salt of manganese(II) complex of diethylenetriaminepentaacetic acid.

39.3 g (=100 mmoles) of diethylenetriaminepentaacetic acid are suspended in 100 ml of water p.i. under nitrogen and mixed with 11.5 g of manganese(II) carbonate. It is heated to 95° C. and 300 ml of 1N sodium hydroxide solution are added drop by drop. The neutral solution is sterilized by filtering and put into ampoules.

EXAMPLE 53

Composition of a powder for protection of a suspension

| | |
|---|---|
| 4.000 g | gadolinium (III) complex of diethylenetriaminepentaacetic acid (water content 8.0%) |
| 3.895 g | saccharose |
| 0.100 g | polyoxyethylenepolyoxypropylene polymer |
| 0.005 g | aromatics |
| 8.000 g | |

EXAMPLE 54

Production of a solution of the gadolinium(III) complex of the conjugate of diethylenetriaminepentaacetic acid with human serum albumin 10 mg of 1,5-bis(2,6-dioxomorpholino)-3-azapentane-3-acetic acid are added to 20 ml of a solution of 3 mg of protein in 0.05 molar sodium bicarbonate buffer (pH 7-8). It is allowed to stir for 30 minutes at room temperature and then dialyzed against a 0.3 molar sodium phosphate buffer. Then 50 mg of gadolium(III) acetate are added and purified by gel chromatography in a Sephadex G25 column. The resulting fraction is sterilized by filtering and put into Multivials. A storable dry product is obtained by freeze-drying.

The solution of the corresponding complex conjugate is obtained in a similar way with immunoglobulin.

EXAMPLE 55

Production of a solution of the gadolium(III) complex of the conjugate of diethylenetriaminepentaacetic acid (DTPA) with monoclonal antibodies 1 mg of a mixed DTPA-anhydride (obtained, for example, from DTPA and isobutyl chloroformate) is added to 20 μl of a solution of 0.3 mg of monoclonal antibodies in 0.05 molar sodium bicarbonate buffer (pH 7-8) and stirred for 30 minutes at room temperature. It is dialyzed against 0.3 molar sodium phosphate buffer and the resulting antibody fraction is mixed with 2 mg of the gadolinium(III) complex of ethylenediaminetetraacetic acid (EDTA). After purification by gel chromatography with Sephadex G25, the solution sterilized by filtering is put in Multivials and freeze-dried.

A solution of the corresponding gadolinium(III) complex of CDTA-antibodies is obtained in a similar way by using the mixed anhydride of trans-1,2-diaminocyclohexanetetraacetic acid (CDTA).

The manganese(II) complex of the antibodies coupled with DTPA or CDTA is obtained in a similar way by using the manganese(II) complex of ethylenediaminetetraacetic acid.

EXAMPLE 56

Production of a solution of the gadolinium(III) complex of the conjugate of 1-phenylethylenediaminetetraacetic acid with immunoglobulin By following the method described in J. Med. Chem. 1974, Vol. 17, p 1307, a 2% solution of protein in a 0.12 molar sodium bicarbonate solution, which contains 0.01 mole of ethylenediaminetetraacetic acid is cooled to +4° C. and mixed drop by drop with the protein equivalent portion of a freshly produced ice-cold diazonium salt solution of 1-(p-aminophenyl)ethylenediaminetetraacetic acid. It is allowed to stir overnight at +4° C. (pH 8.1) and then dialyzed against a 0.1 molar sodium citrate solution. After completion of the dialysis, the solution of the conjugate is mixed with an excess of gadolinium(III) chloride and ultrafiltered to remove ions. Then the solution sterilized by filtering is put into Multivials and freeze-dried.

EXAMPLE 57

Production of a colloidal dispersion of an Mn-CDTA-lipid conjugate 0.1 mmole of distearoylphosphatidylethanolamine and 0.1 mmole of bisanhydride of trans-1,2-diaminocyclohexanetetraacetic acid are stirred in 50 ml of water for 24 hours at room temperature. 0.1 mmole of manganese(II) carbonate is added and restirred for 6 hours at room temperature. After purification with a Sephadex G50 column, the solution sterilized by filtering is put into Multivials and freeze-dried.

A colloidal dispersion of the gadolinium-DTPA-lipid conjugate can be obtained in a similar way with gadolinium(III) oxide.

EXAMPLE 58

Production of liposomes loaded with gadolinium-DTPA

By following the method described in Proc. Natl. Acad. Sci. U.S.A. 75, 4194, a lipid mixture is produced from 75 mole % of egg phosphatidylcholine and 25 mole % of cholesterol as a dry substance. 500 mg of it are dissolved in 30 ml of diethylether and mixed drop by drop in an ultrasonic bath with 3 ml of a 0.1 molar solution of the di-N-methylglucamine salt of gadolinium(III) complex of diethylenetriaminepentaacetic acid in water p.i. After completre addition of the solution, the treatment with ultrasonic waves is continued for 10 more minutes and then concentrated in the Rotavapor. The gelatinous residue is suspended in 0.125 molar sodium chloride solution and is freed of the unencapsulated contrast medium portions by repeated centrifuging (20000 g/20 minutes) at 0° C. Finally, the resulting liposomes are freeze-dried in the Multivial. Application is as a colloidal dispersion in 0.9 percent by weight of sodium chloride solution.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of imaging body tissue in a patient, comprising subjecting the patient to NMR tomography and prior to performing the NMR tomography administering to the patient an effective amount of a pharmaceutical agent for affecting the relaxation times of atoms in body tissue undergoing NMR diagnosis, whereby image contrast is enhanced, said agent comprising an amount, effective to affect such relaxation times, of a paramagnetic, physiologically compatible chelate complex of an ion of a lanthanide element of atomic numbers 58–70; and a pharmaceutically acceptable carrier.

2. A method of imaging body tissue in a patient, comprising subjecting the patient to NMR tomography and prior to performing the NMR tomography administering to the patient an effective amount of a pharmaceutical agent for affecting the relaxation times of atoms in body tissues undergoing NMR diagnosis, whereby image contrast is enhanced, said agent comprising an amount, effective to affect such relaxation times, of a paramagnetic, physiologically compatible chelate complex of an ion and, as a ligand, an acyclic or cyclic complexing agent containing organic nitrogen, phosphorus, oxygen or sulfur, the complexed ion being an ion of a lanthanide element of atomic numbers 58–70; and a pharmaceutically acceptable carrier.

3. A method of enhancing NMR imageability of a patient comprising administering to the patient an amount, effective to enhance NMR image contrast, of a physiologically compatible chelate complex of a paramagnetic ion.

4. A method of enhancing NMR imageability of a patient comprising administering to the patient an amount, effective to enhance NMR image contrast, of a physiologically compatible chelate complex of a paramagnetic ion having as a ligand a complexing agent containing organic nitrogen, phosphorous, oxygen or sulfur.

5. A method of claim 3, wherein the complex is formulated together with a pharmaceutically acceptable carrier.

6. A method of claim 4, wherein the complex is formulated together with a pharmaceutically acceptable carrier.

7. A method of claim 5, wherein said ion is an element of atomic numbers 58–70.

8. A method of claim 6, wherein said ion is an element of atomic numbers 58–70.

9. A method of claim 5, wherein said ion is an element of atomic numbers 21–29, 42 or 44.

10. A method of claim 6, wherein said ion is an element of atomic numbers 21–29, 42 or 44.

11. A method of conducting NMR imaging, comprising NMR imaging a patient to whom there has been administered an amount effective to enhance NMR image contrast of a physiologically compatible chelate complex of a paramagnetic ion, whereby an NMR image of enhanced contrast is obtained.

12. A method of conducting NMR imaging, comprising NMR imaging a patient to whom there has been administered an amount effective to enhance NMR image contrast of a physiologically compatible chelate complex of a paramagnetic ion having as ligand a complexing agent containing organic nitrogen, phosphorous, oxygen or sulfur, whereby an NMR image of enhanced contrast is obtained.

13. A method of claim 11, wherein the complex is formulated together with a pharmaceutically acceptable carrier.

14. A method of claim 12, wherein the complex is formulated together with a pharmaceutically acceptable carrier.

15. A method of claim 13, wherein said ion is an element of atomic numbers 58–70.

16. A method of claim 14, wherein said ion is an element of atomic numbers 58–70.

17. A method of claim 13, wherein said ion is an element of atomic numbers 21–29, 42 or 44.

18. A method of claim 14, wherein said ion is an element of atomic numbers 21–29, 42 or 44.

19. A method of claim 1, wherein the paramagnetic ion is Gd(III).

20. A method of claim 2, wherein the paramagnetic ion is Gd(III).

21. A method of claim 5, wherein the paramagnetic ion is Gd(III).

22. A method of claim 6, wherein the paramagnetic ion is Gd(III).

23. A method of claim 13, wherein the paramagnetic ion is Gd(III).

24. A method of claim 14, wherein the paramagnetic ion is Gd(III).

25. A method of claim 5, wherein the paramagnetic ion is Mn(II).

26. A method of claim 6, wherein the paramagnetic ion is Mn(II).

27. A method of claim 13, wherein the paramagnetic ion is Mn(II).

28. A method of claim 14, wherein the paramagnetic ion is Mn(II).

29. A method of claim 5, wherein the paramagnetic ion is iron.

30. A method of claim 6, wherein the paramagnetic ion is iron.

31. A method of claim 13, wherein the paramagnetic ion is iron.

32. A method of claim 14, wherein the paramagnetic ion is iron.

33. A method of claim 1, wherein the paramagnetic ion is chelated by an aminopolycarboxylic acid.

34. A method of claim 2, wherein the paramagnetic ion is chelated by an aminopolycarboxylic acid.

35. A method of claim 5, wherein the paramagnetic ion is chelated by an aminopolycarboxylic acid.

36. A method of claim 6, wherein the paramagnetic ion is chelated by an aminopolycarboxylic acid.

37. A method of claim 13, wherein the paramagnetic ion is chelated by an aminopolycarboxylic acid.

38. A method of claim 14, wherein the paramagnetic ion is chelated by an aminopolycarboxylic acid.

39. A method of claim 1, wherein no free acid or free base groups are present in the chelate complex.

40. A method of claim 2, wherein no free acid or free base groups are present in the chelate complex.

41. A method of claim 5, wherein no free acid or free base groups are present in the chelate complex.

42. A method of claim 6, wherein no free acid or free base groups are present in the chelate complex.

43. A method of claim 13, wherein no free acid or free base groups are present in the chelate complex.

44. A method of claim 14, wherein no free acid or free base groups are present in the chelate complex.

45. A method of claim 1, wherein a free acid or a free base group is present in the chelate complex.

46. A method of claim 2, wherein a free acid or a free base group is present in the chelate complex.

47. A method of claim 5, wherein a free acid or a free base group is present in the chelate complex.

48. A method of claim 6, wherein a free acid or a free base group is present in the chelate complex.

49. A method of claim 13, wherein a free acid or a free base group is present in the chelate complex.

50. A method of claim 14, wherein a free acid or a free base group is present in the chelate complex.

51. A method of claim 1, wherein a free acid or a free base group of the chelate complex is in the form of a salt thereof with an inorganic or organic base or acid.

52. A method of claim 2, wherein a free acid or a free base group of the chelate complex is in the form of a salt thereof with an inorganic or organic base or acid.

53. A method of claim 5, wherein a free acid or a free base group of the chelate complex is in the form of a salt thereof with an inorganic or organic base or acid.

54. A method of claim 6, wherein a free acid or a free base group of the chelate complex is in the form of a salt thereof with an inorganic or organic base or acid.

55. A method of claim 13, wherein a free acid or a free base group of the chelate complex is in the form of a salt thereof with an inorganic or organic base or acid.

56. A method of claim 14, wherein a free acid or a free base group of the chelate complex is in the form of a salt thereof with an inorganic or organic base or acid.

57. A method of claim 1, wherein the paramagnetic ion is chelated by an open-chain chelating agent.

58. A method of claim 1, wherein the paramagnetic ion is chelated by an open-chain chelating agent.

59. A method of claim 5, wherein the paramagnetic ion is chelated by an open-chain chelating agent.

60. A method of claim 6, wherein the paramagnetic ion is chelated by an open-chain chelating agent.

61. A method of claim 13, wherein the paramagnetic ion is chelated by an open-chain chelating agent.

62. A method of claim 14, wherein the paramagnetic ion is chelated by an open-chain chelating agent.

63. A method of claim 1, wherein the paramagnetic ion is chelated by a cyclic chelating agent.

64. A method of claim 2, wherein the paramagnetic ion is chelated by a cyclic chelating agent.

65. A method of claim 5, wherein the paramagnetic ion is chelated by a cyclic chelating agent.

66. A method of claim 6, wherein the paramagnetic ion is chelated by a cyclic chelating agent.

67. A method of claim 13, wherein the paramagnetic ion is chelated by a cyclic chelating agent.

68. A method of claim 14, wherein the paramagnetic ion is chelated by a cyclic chelating agent.

69. A method of claim 1, wherein said chelate complex is both a salt of said paramagnetic ion and the chelate complexing agent thereof, and also a salt with an inorganic or organic base or acid.

70. A method of claim 2, wherein said chelate complex is both a salt of said paramagnetic ion and the chelate complexing agent thereof, and also a salt with an inorganic or organic base or acid.

71. A method of claim 5, wherein said chelate complex is both a salt of said paramagnetic ion and the chelate complexing agent thereof, and also a salt with an inorganic or organic base or acid.

72. A method of claim 6, wherein said chelate complex is both a salt of said paramagnetic ion and the chelate complexing agent thereof, and also a salt with an inorganic or organic base or acid.

73. A method of claim 13, wherein said chelate comlex is both a salt of said paramagnetic ion and the chelate complexing agent thereof, and also a salt with an inorganic or organic base or acid.

74. A method of claim 14, wherein said chelate complex is both a salt of said paramagnetic ion and the chelate complexing agent thereof, and also a salt with an inorganic or organic base or acid.

75. A method of claim 1, wherein said chelate complex is only a salt of said paramagnetic ion and the chelate complexing agent thereof and not also a salt with an inorganic or organic base or acid.

76. A method of claim 2, wherein said chelate complex is only a salt of said paramagnetic ion and the chelate complexing agent thereof and not also a salt with an inorganic or organic base or acid.

77. A method of claim 5, wherein said chelate complex is only a salt of said paramagnetic ion and the chelate complexing agent thereof and not also a salt with an inorganic or organic base or acid.

78. A method of claim 6, wherein said chelate complex is only a salt of said paramagnetic ion and the chelate complexing agent thereof and not also a salt with an inorganic or organic base or acid.

79. A method of claim 13, wherein said chelate complex is only a salt of said paramagnetic ion and the chelate complexing agent thereof and not also a salt with an inorganic or organic base or acid.

80. A method of claim 14, wherein said chelate complex is only a salt of said paramagnetic ion and the chelate complexing agent thereof and not also a salt with an inorganic or organic base or acid.

81. A method of claim 1, wherein the chelate complex molecule consists of a single paramagnetic ion chelated by a chelating agent which optionally is a salt with an inorganic or organic base or acid.

82. A method of claim 2, wherein the chelate complex molecule consists of a single paramagnetic ion chelated by a chelating agent which optionally is a salt with an inorganic or organic base or acid.

83. A method of claim 5, wherein the chelate complex molecule consists of a single paramagnetic ion chelated by a chelating agent which optionally is a salt with an inorganic or organic base or acid.

84. A method of claim 6, wherein the chelate complex molecule consists of a single paramagnetic ion chelated by a chelating agent which optionally is a salt with an inorganic or organic base or acid.

85. A method of claim 13, wherein the chelate complex molecule consists of a single paramagnetic ion chelated by a chelating agent which optionally is a salt with an inorganic or organic base or acid.

86. A method of claim 14, wherein the chelate complex molecule consists of a single paramagnetic ion chelated by a chelating agent which optionally is a salt with an inorganic or organic base or acid.

87. A method of claim 1, wherein the chelate complex is not bound to a protein.

88. A method of claim 2, wherein the chelate complex is not bound to a protein.

89. A method of claim 5, wherein the chelate complex is not bound to a protein.

90. A method of claim 6, wherein the chelate complex is not bound to a protein.

91. A method of claim 13, wherein the chelate complex is not bound to a protein.

92. A method of claim 14, wherein the chelate complex is not bound to a protein.

93. A method of claim 29, wherein the paramagnetic ion is Fe(II).

94. A method of claim 30, wherein the paramagnetic ion is Fe(II).

95. A method of claim 31, wherein the paramagnetic ion is Fe(II).

96. A method of claim 32, wherein the paramagnetic ion is Fe(II).

97. A method of imaging body tissue in a patient, comprising subjecting the patient to NMR tomography and prior to performing the NMR tomography administering to the patient an effective amount of a pharmaceutical agent for affecting the relaxation times of atoms in body tissue undergoing NMR diagnosis, whereby image contrast is enhanced, said agent comprising an amount, effective to affect such relaxation times, of a paramagnetic, physiologically compatible chelate complex of an ion of a transition metal of atomic numbers 21-29, 42, or 44; and a pharmaceutically acceptable carrier.

98. A method of imaging body tissue in a patient, comprising subjecting the patient to NMR tomography and prior to performing the NMR tomography administering to the patient an effective amount of a pharmaceutical agent for affecting the relaxation times of atoms in body tissues undergoing NMR diagnosis, whereby image contrast is enhanced, said agent comprising an amount, effective to affect such relaxation times, of a paramagnetic physiologically compatible chelate complex of an ion and, as a ligand, an acyclic or cyclic complexing agent containing organic nitrogen, phosphorus, oxygen or sulfur, the complexed ion being an ion of a transition metal of atomic numbers 21-29, 42, or 44; and a pharmaceutically acceptable carrier.

99. A method of claim 97, wherein the paramagnetic ion is Mn(II).

100. A method of claim 98, wherein the paramagnetic ion is Mn(II).

101. A method of claim 97, wherein the paramagnetic ion is iron.

102. A method of claim 98, wherein the paramagnetic ion is iron.

103. A method of claim 97, wherein the paramagnetic ion is chelated by an aminopolycarboxylic acid.

104. A method of claim 98, wherein the paramagnetic ion is chelated by an aminopolycarboxylic acid.

105. A method of claim 97, wherein no free acid or free base groups are present in the chelate complex.

106. A method of claim 98, wherein no free acid or free base groups are present in the chelate complex.

107. A method of claim 97, wherein a free acid or a free base group is present in the chelate complex.

108. A method of claim 98, wherein a free acid or a free base group is present in the chelate complex.

109. A method of claim 97, wherein a free acid or a free base group of the chelate complex is in the form of a salt thereof with an inorganic or organic base or acid.

110. A method of claim 98, wherein a free acid or a free base group of the chelate complex is in the form of a salt thereof with an inorganic or organic base or acid.

111. A method of claim 97, wherein the paramagnetic ion is chelated by an open-chain chelating agent.

112. A method of claim 98, wherein the paramagnetic ion is chelated by an open-chain chelating agent.

113. A method of claim 97, wherein the paramagnetic ion is chelated by a cyclic chelating agent.

114. A method of claim 98, wherein the paramagnetic ion is chelated by a cyclic chelating agent.

115. A method of claim 97, wherein said chelate complex is both a salt of said paramagnetic ion and the chelate complexing agent thereof, and also a salt with an inorganic or organic base or acid.

116. A method of claim 98, wherein said chelate complex is both a salt of said paramagnetic ion and the chelate complexing agent thereof, and also a salt with an inorganic or organic base or acid.

117. A method of claim 97, wherein said chelate complex is only a salt of said paramagnetic ion and the chelate complexing agent thereof and not also a salt with an inorganic or organic base or acid.

118. A method of claim 98, wherein said chelate complex is only a salt of said paramagnetic ion and the chelate complexing agent thereof and not also a salt with an inorganic or organic base or acid.

119. A method of claim 97, wherein the chelate complex molecule consists of a single paramagnetic ion chelated by a chelating agent which optionally is a salt with an inorganic or organic base or acid.

120. A method of claim 98, wherein the chelate complex molecule consists of a single paramagnetic ion chelated by a chelating agent which optionally is a salt with an inorganic or organic base or acid.

121. A method of claim 97, wherein the chelate complex is not bound to a protein.

122. A method of claim 98, wherein the chelate complex is not bound to a protein.

123. A method of claim 101, wherein the paramagnetic ion is Fe(II).

124. A method of claim 102, wherein the paramagnetic ion is Fe(II).

125. A method of claim 1, wherein the patient is a human.

126. A method of claim 2, wherein the patient is a human.

127. A method of claim 5, wherein the patient is a human.

128. A method of claim 6, wherein the patient is a human.

129. A method of claim 13, wherein the patient is a human.

130. A method of claim 14, wherein the patient is a human.

131. A method of claim 97, wherein the patient is a human.

132. A method of claim 98, wherein the patient is a human.

133. A method of enhancing an NMR image, comprising obtaining an enhanced NMR image by NMR imaging a human to whom there has been administered an amount, effective to enhance NMR image contrast, of a physiologically compatible chelate complex of a paramagnetic ion.

134. A method of claim 133, wherein the complex is formulated together with a pharmaceutically acceptable carrier.

135. A method of claim 134, wherein said ion is an element of atomic numbers 58-70.

136. A method of claim 134, wherein said ion is an element of atomic numbers 21-29, 42 or 44.

137. A method of claim 134, wherein the paramagnetic ion is Gd(III).

138. A method of claim 134, wherein the paramagnetic ion is Mn(II).

139. A method of claim 134, wherein the paramagnetic ion is iron.

140. A method of claim 134, wherein the paramagentic ion is Fe(II).

141. A method of claim 134, wherein the paramagnetic ion is chelated by an aminopolycarboxylic acid.

142. A method of claim 134, wherein no free acid or free base groups are present in the chelate complex.

143. A method of claim 134, wherein a free acid or a free base group is present in the chelate complex.

144. A method of claim 134, wherein a free acid or a free base group of the chelate complex is in the form of a salt thereof with an inorganic or organic base or acid.

145. A method of claim 134, wherein the paramagnetic ion is chelated by an open-chain chelating agent.

146. A method of claim 134, wherein the paramagnetic ion is chelated by a cyclic chelating agent.

147. A method of claim 134, wherein said chelate complex is both a salt of said paramagnetic ion and the chelate complexing agent thereof, and also a salt with an inorganic or organic base or acid.

148. A method of claim 134, wherein said chelate complex is only a salt of said paramagnetic ion and the chelate complexing agent thereof and not also a salt with an inorganic or organic base or acid.

149. A method of claim 134, wherein the chelate complex molecule consists of a single paramagnetic ion chelated by a chelating agent which optionally is a salt with an inorganic or organic base or acid.

150. A method of claim 134, wherein the chelate complex is not bound to a protein.

151. A method of claim 1, wherein the chelate complex is nonionic.

152. A method of claim 2, wherein the chelate complex is nonionic.

153. A method of claim 5, wherein the chelate complex is nonionic.

154. A method of claim 6, wherein the chelate complex is nonionic.

155. A method of claim 13, wherein the chelate complex is nonionic.

156. A method of claim 14, wherein the chelate complex is nonionic.

157. A method of claim 23, wherein the chelate complex is nonionic.

158. A method of claim 27, wherein the chelate complex is nonionic.

159. A method of claim 31, wherein the chelate complex is nonionic.

160. A method of claim 61, wherein the chelate complex is nonionic.

161. A method of claim 67, wherein the chelate complex is nonionic.

162. A method of claim 97, wherein the chelate complex is nonionic.

163. A method of claim 98, wherein the chelate complex is nonionic.

164. A method of claim 133, wherein the chelate complex is nonionic.

165. A method of claim 137, wherein the chelate complex is nonionic.

166. A method of claim 138, wherein the chelate complex is nonionic.

167. A method of claim 139, wherein the chelate complex is nonionic.

168. A method of claim 145, wherein the chelate complex is nonionic.

169. A method of claim 146, wherein the chelate complex is nonionic.

* * * * *

UNITED STATES PATENT AND TRADEMARK OFFICE
CERTIFICATE OF CORRECTION

PATENT NO. : 4,963,344

DATED : October 16, 1990

INVENTOR(S) : Heinz Gries et al

It is certified that error appears in the above-identified patent and that said Letters Patent is hereby corrected as shown below:

Column 26, Claim 58, Line 31:

Reads: "A method of claim 1, wherein the paramagnetic"
   Should read:--A method of claim 2, wherein the paramagnetic--

Column 30, Claim 164, Line 56:

Reads: "A method of claim 133, wherein the chelate"
   Should Read:--A method of claim 134, wherein the chelate--

Signed and Sealed this

Tenth Day of March, 1992

Attest:

HARRY F. MANBECK, JR.

*Attesting Officer*     *Commissioner of Patents and Trademarks*

REEXAMINATION CERTIFICATE (1781st)

United States Patent [19]
Gries et al.

[11] B1 4,963,344
[45] Certificate Issued Aug. 25, 1992

[54] METHOD TO ENHANCE NMR IMAGING USING CHELATED PARAMAGNETIC IONS

[75] Inventors: Heinz Gries; Douwe Rosenberg; Hann-Joachim Weinmann; Ulrich Speck; Wolfgang Mutzel; Georg-Alexander Hoyer; Heinrich Pfeiffer, all of Berlin, Fed. Rep. of Germany

[73] Assignee: Schering Aktiengesellschaft, Berlin & Bergkamen, Fed. Rep. of Germany

Reexamination Request:
No. 90/002,281, Feb. 14, 1991

Reexamination Certificate for:
Patent No.: 4,963,344
Issued: Oct. 16, 1990
Appl. No.: 370,139
Filed: Jun. 23, 1989

[30] Foreign Application Priority Data

Jul. 24, 1981 [DE] Fed. Rep. of Germany ....... 3129906
Jan. 21, 1983 [DE] Fed. Rep. of Germany ....... 3302410
Jan. 11, 1984 [DE] Fed. Rep. of Germany ....... 3401057

[51] Int. Cl.[5] ...................... H61K 49/00; G01N 31/00
[52] U.S. Cl. .............................. 424/9; 128/653 CA; 128/654; 436/173; 436/806
[58] Field of Search ............ 128/653 CA, 654; 424/9; 436/173, 806

[56] References Cited

U.S. PATENT DOCUMENTS

| | | | |
|---|---|---|---|
| 3,252,082 | 5/1966 | Hiller | 324/0.5 |
| 3,818,061 | 6/1974 | Belanger et al. | 260/429.2 |
| 3,932,805 | 1/1976 | Abe et al. | 324/0.5 A |
| 4,066,743 | 1/1978 | Kneller | 424/5 |
| 4,972,837 | 11/1990 | Engelstad et al. | 120/654 |

FOREIGN PATENT DOCUMENTS

| | | |
|---|---|---|
| 0169299 | 1/1986 | European Pat. Off. |
| 3129906C2 | 2/1983 | Fed. Rep. of Germany |
| 2159411 | 6/1973 | France |
| 48-56190 | 8/1973 | Japan |

OTHER PUBLICATIONS

Herman, R., "A chemical clue to disease", New Scientist, Mar. 15, 1979 pp. 874–877.
Haley, T. J., "Chapter 40 Toxicity", *Handbook on the Physics and Chemistry of Rare Earths*, North-Holland Pub. Co., 1979, pp. 553–585.
CA 78(8): 48753k, Kornen et al. (1972).
CA 87(6): 44916d, Mitrofanova et al. (1977).
Reuben, Jacques, "Chapter 39 Bioinorganic Chemistry: Lanthanides as Probes in Systems of Biological Interest", Handbook on the Physics and Chemistry of Rare Earths, North-Holland Pub. Co., 1979, pp. 515–552.
Martell et al., Critical Stability Constants, vol. 1: Amino Acids (1974) Plenum Press, New York and London, pp. 207, 288, 283, 238, 303, 304, 305, 96.
Jones et al., "Therapeutic Chelating Agents", Journal of Chemical Education, vol. 53, No. 6, Jun. 1976, pp. 342–347.
Bloch et al., "A Nuclear Magnetic Resonance Relaxation Study of Iron(III) EDTA in Aqueous Solution", Inorganic Nuclear Chem., vol. 42, pp. 693–699, 1980.
Alsaadi et al., "Hydration of Complexone—Complexes of Lanthanide Cations", J. Chem. Soc., Dalton Trans., pp. 2151–2154 (1980).
Reuben, J., "Gadolinium(III) as a Paramagnetic Probe for Proton Relaxation Studies of Biological Macromolecules, Binding to Bovine Serum Albumin" Biochemistry, vol. 10, No. 15, 1971, pp. 2834–2839.
Dwek et al., "The Lanthanide Cations as Probes in Biological Systems, Proton Relaxation Enhancement Studies for Model Systems and Lysozyme" Eur. J. Biochem. 21 (1971) 204–209.
Oakes et al., "Structure of Mn-EDTA$^{2-}$ Complex in Aqueous Solution by Relaxation Nuclear Magnetic Resonance, J. Chem. Soc., Faraday Trans. 2, 1981, 77, 299–308.
Runge et al. "Paramagnetic NMR Contrast Agents Development and Evaluation" Investigative Radiology Sep.–Oct 1984, vol. 19, pp. 408–415.
Rosoff et al., "Effect of Chelating Agents on the Removal of Yttrium and Lanthanum from Man", Health Physics, vol. 6, 1961, pp. 1977–1982.
Japanese Patent Appln. No. 127810/1982, Japanese Patent Office Action, Mailed: Nov. 17, 1989.
Bailar, Jr., et al., *Comprehensive Inorganic Chemistry*, Pergamon Press (1973) pp. 11 and 29.
Martell et al., Critical Stability Constants, vol. 1: Amino Acids, Plenum Press, New York and London, pp. 281–285 (1974).
Dwyer et al, Chelating Agents and Metal Chelates, Academic Press, New York and London, 1964, pp. 29 and 292.
Kornev et al., "Complexes of Iron(III) and Indium(III) with beta-hydroxyethyliminodiacetic acid", Zh. Fiz. Khim. 46 (10), pp. 2485–2487 (1972).
Mitrofanova et al., "Spectrographic Study of Complexes of Neodymium with (hydroxyethyl)iminodiacetic acid", Zh. Neorg. Khim. 22(5), pp. 1235–1238 (1977).
Dreisbach, R. H., *Handbook of Poisoning: Diagnosis Treatment*, 8th Edition Lange Medical Publications, Los Altos, Calif. 1974, pp. 80–85.
Levine, W., "Section XI Heavy Metals and Heavy-Metal Antagonists", Chapter 45 Heavy-Metal Antagonists, *The Pharmacological Basis of Therapeutics*, 5th Ed., MacMillan Pub., N.Y., 1975, pp. 912, 915–919.
Essentials of Molecular Pharma., pp. 83, 307–311 (1970).
Goldstein et al., Principles of Drug Action: The Basis of Pharmacology, 2nd Edition, John Wiley & Sons, N.Y., pp. 400–403.
Spencer, H., "Studies of the Effect of Chelating Agents in Man", Annals New York Academy of Sciences, 88, pp. 435–445–449 (1960).
Stacy et al., "Chromium-51 Ethylenediaminetetraacetate for Estimation of Glomerular Filtration Rate", Science, vol. 152, pp. 1076-1077, May 20, 1966.
Bianchi et al., "$^{131}$I-hypaque and $^{140}$La-DTPA for the measurement of glomerular filtration rate in dog", N. Nucl. Biol. Med., 12, pp. 117-120, 1968.
James, Jr. et al., "$^{169}$Ytterbium Diethylenetriaminepentaacetic Acid ($^{169}$Yb DTPA)-A versatile Radiopharmaceutical", Journal de l'Association Canadienne des Radiologistes, vol. 22, Jun. 1971, pp. 136-143.
La Mar et al., *NMR of Paramagnetic Molecules*, Academic Press, N.Y. 1973 pp. 53-83, 185-199.
Ahrens et al., "A comparative Study of the Toxic Effects of Calcium and Chromium Chelates of Ethylenediaminetetraacetate in the Dog", Toxicology and Applied Pharmacology, 18, 10-25 (1971).
Cotzias, G., "Manganese in Health and Disease", Physiolog. Reviews, vol. 38, Jul. 1958, pp. 503-532.
Haley, T. J., "Pharmacology and Toxicology of the Rare Earth Elements", Journal of Pharmaceutical Sciences, May 1965, vol. 54, No. 5, pp. 663-670.
CA 63:7704b (1965) (Wright).
CA 85:160192x (1976) (Lehn).
CA 83:10965c (1959) (Sawyer).
CA 53:56092c (1966) (Voitovich).
CA 86:130665g (1977) (Elgavish et al.).
CA 44:2882i (1949) (Johanason).
CA 69:5682h (1967) (Kabachnik).
Carson et al., "The Thermodynamics of the Formation of Complexes between Diethylenetriaminepenta-acetic Acid and the Lanthanide Ions", J. Chem. Soc. (A), 1968, pp. 1384-1386.
Arvela, P., Toxicity of Rare-Earths 011334, Prog. Pharmacol. 2, 1979, pp. 73-114.
Lauterbur et al., Program and Abstracts, Experimental 19th NMR Conference Apr. 16-20, 1978, "Water Proton Relaxation by Manganous Ion in Tissues", Abstract B-19.
Lauterbur, "Image Formation by Induced Local Interactions: Examples Employing . . . ", Nature, vol. 242, No. 5394, pp. 190-191, Mar. 16, 1973.
Lauterbur et al., Abstracts for Sixth Int'l Biophysics Congress, Kyoto, Japan, Sep. 3-9 (1978), p. 12, Symposium 20 (Sep. 4, 1978).
Lauterbur et al., "NMR Zeugmatographic Imaging of Organs and Organisms," from Stereodynamics of Molecular Systems, Sarma (editor), Pergamon Press: Oxford, pp. 453-456 (1979).
Bloch et al., "The Nuclear Induction Experiment", Physical Review, vol. 70 Nos. 7 and 8, Oct. 1 and 15, 1946, pp. 474-485.
Solomon, "Relaxation Processes in a System of Two Spins", Physical Review vol. 99, No. 2, Jul. 15, 1955, pp. 559-565.
James, *Nuclear Magnetic Resonance in Biochemistry*, Academic Press, New York, p. 179 (1975).
Anderegg, *Critical Survey of Stability Constants of EDTA Complexes*, Pergamon Press, IUPAC Chemical Data Series—No. 14, pp. 1-36 (1977).
Rubin et al., "Chelates as Possible Contrast Media", 78, Annals New York Academy of Sciences, pp. 764-778 (1959).
Dwek, Nuclear Magnetic Resonance (NMR) in Biochemistry, "Examples of Relaxation Studies of Paramagnetic Metal Macromolecular Complexes," Chapters 9-11, Clarendon Press Oxford, pp. 174-284 (1973).
*Physicians' Desk Reference:* For Radiology and Nuclear Medicine, Blaufox et al. (editors), 1976/77, pp. 77-79.
Dwek, *Nuclear Magnetic Resonance (NMR) in Biochemistry*, "*Examples of Relaxation Studies of Paramagnetic Metal Macromolecule Complexes,*" *Chapters 9-11, Clarendon Press, Oxford, pp. 174-284 (1973).*
*Physicians' Desk Reference:* For Radiology and Nuclear Medicine, Blaufox et al. (editors), 1976/77, pp. 77-79.
Lauterbur, "Progress in NMR Zeugmatographic Imaging", Phil. Trans. R. Soc. London, B 29, pp. 483-487 (1980).
Kniseley et al., "Delineation of Active Marrow by Whole-Body Scanning with Radioactive Colloids", J. of Nuc. Med. 7:575-582 (1966).
Doyle et al., "Relaxation Rate Enhancement Observed In Vivo by NMR Imaging", Proceedings of NMR Imaging Symposium, Nashville, Tenn., Oct. 26-27, 1980, abstracted in J. of Comput, Assist. Tomography 5(2):295-96 (1981).
J. Tripod, CA 62:3309h (1965).
C. Nofre et al., CA 69:3314c (1964).
J. King et al., "On the $T_1/T_2$ Ratio for Protons in Aqueous $Mn^{++}$ Solutions", J. Chem. Physics, vol. 29, No. 4, pp. 787-791 (Oct. 1958).
Reuben et al., Proc. Rare Earth Res. Conf., 12th, col. 1, 25-26 (1976).

*Primary Examiner*—Richard L. Raymond

[57] ABSTRACT

Agents useful for influencing the relaxation times in NMR diagnostics, contain at least one paramagnetic, physiologically compatible complex salt comprising a chleate from an open-chain or cyclic complex-forming compound containing organic nitrogen, phosphorus, oxygen and/or sulfur, and a complexed ion of the lanthanide elements of atomic number 57-70 or of the transition metals of atomic numbers 21-29, 42 and 44, and, optionally, an inorganic or organic base or acid.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 23, after last line, specification from earliest parent is added.

The following is the text of U.S. Ser. No. 401,594, filed on July 26, 1982.

BACKGROUND OF THE INVENTION

*Several physical diagnostic methods are customary in medical practice which can be executed without any or with only minor operative interventions. These include, for example, subjecting the body to X-ray radiation, performing scintigraphy, and performing sonography. All of these methods either carry a health risk or are limited in their range of application. Thus, a patient is exposed to ionizing radiation when subjected to X-ray techniques and to scintigraphy so that these methods cannot be utilized with any desired frequency or cannot be employed at all in certain risk categories, such as, for example, infants and pregnant women. Although sonography does not exhibit the aforementioned drawbacks, its range of application is very restricted, especially in the cranial area.*

*Since it has not been possible heretofore to completely overcome the above-described disadvantages in spite of great expenditures in research, efforts have been made to provide imaging procedures not possessing these disadvantages yet yielding a comparable wealth of information for diagnosis.*

*One of these imaging processes is nuclear-spin tomography (spin imaging, "zeugmatography") based on the physical effect of so-called nuclear spin resonance (nuclear magnetic resonance, NMR). This diagnostic method makes it possible to obtain section images of the living body and to view metabolic processes without the use of ionizing radiation. Nuclear magnetic resonance effects are displayed by atomic nuclei which possess a magnetic moment, such as hydrogen which is present primarily as water in biological tissue. Such nuclei are aligned in a strong external magnetic field. By a high frequency pulse (resonant frequency), the aligned atomic nuclei are excited out of their equilibrium position, to which latter they return with a characteristic speed. The duration of return to the equilibrium condition, the so-called relaxation time, yields information on the energy level of the atoms and their interaction with their environment.*

*The imaging obtained by measuring proton density and/or relaxation times is of high diagnostic value and yields information on the water content and the condition of the tissue being studied. Thus, tumor tissue, for example, exhibits longer relaxation times than healthy comparison tissue [A. Ganssen et al., Computertomographie 1 [Computerized Tomography 1]: 2-10 (1981); Georg Thieme Publishers, Stuttgart, New York].*

*It has now been found that paramagnetic ions, such as, for example, $Mn^{2+}$ (manganese) affect the relaxation times and thus enhance the information content. (Dennis R. Burton et al., Progress in NMR Spectroscopie, Vol. 13, pp. 1-45: Proton Relaxation Enhancement (PRE) in Biochemistry; A critical Survey; F. H. Doyle et al., J. Comput. Assist. Tomogr., vol. 5, No. 2, pp. 295-296: Relaxation rate enhancement observed in vivo by NMR imaging.)*

*The heavy metal salt solutions heretofore used for this purpose with experimental animals are, however, unsuitable for intravenous administration to human patients due to their high toxicity. Consequently, there are sought paramagnetic compounds which are well compatible and favorably influence the imaging process. The latter can be achieved, for example, by greatly reducing, if possible in an organ-specific fashion, the spin-lattice relaxation time $T_1$ while simultaneously keeping the spin-spin relaxation time $T_2$ maximally constant.*

SUMMARY OF THE INVENTION

*Accordingly, it is an object of this invention to provide such paramagnetic compounds, useful as image enhancers in NMR tomography, which have such desirable properties and lack or significantly ameliorate such disadvantages.*

*Upon further study of the specification and appended claims, further objects and advantages of this invention will become apparent to those skilled in the art.*

*These objects have now been achieved based on the finding that the desired detoxification of the otherwise toxic metallic salts can be accomplished without adversely affecting the paramagnetic properties by complexing them. The maintenance of paramagnetism is surprising, inasmuch as, by complexing, the distribution of the d or f electrons over the d or f orbitals is, as is known, altered.*

*The present invention thus relates to novel agents for influencing the relaxation times in NMR diagnostics, containing at least one paramagnetic, physiologically compatible salt of a complex comprising open-chain or cyclic complex-forming compounds as ligands containing organic nitrogen, phosphorus, oxygen and/or sulfur; ions of the lanthanide elements of atomic numbers 57-70 or ions of the transition metal elements of atomic numbers 21-29, 42, and 44; and, optionally, an inorganic or organic base or acid.*

*Aminopolycarboxylic acids are employed, for example, for complex formation with the metal cations. Suitable aminopolycarboxylic acids are all compounds of this class of substances capable of forming physiologically compatible chelate complexes, such as, for example:*

| | |
|---|---|
| *nitrilotriacetic acid (NTA),* | (I) |
| *N,N,N',N'-ethylenediaminetetraacetic acid (EDTA),* | (II) |
| *N-hydroxyethyl-N,N',N'-ethylenediaminetriacetic acid (HEDTA),* | (III) |
| *N,N,N',N'',N''-diethylenetriaminepentaacetic acid (DTPA)* | (IV) |
| or | |
| *N-hydroxyethyliminodiacetic acid* | (V) |

*EDTA (II) and DTPA (IV) are preferred.*

*Also, suitable complexing agents are amines of Formula VI*

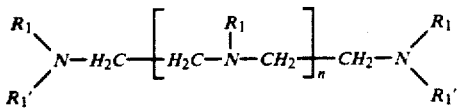

(VI)

wherein $R_1$ and $R_1'$ are identical or different and each is hydrogen or alkyl or 1–4 carbon atoms and n is an integer of 0–4;

macrocyclic compounds of Formula VII

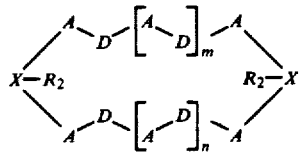

(VII)

wherein each $R_2$ independently is hydrogen, a hydrocarbon residue, an alkoxycarbonyl residue, or both residues $R_2$ together form a group of Formula VIIa

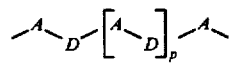

(VIIa)

wherein, throughout the above, each A independently is a hydrocarbon residue, each X is independently a nitrogen or phosphorus atom, each D independently is an oxygen or sulfur atom, a group of the formula $>N-R$ (wherein each R independently is hydrogen or a hydrocarbon residue), or a hydrocarbon residue, with the provios that at least two of the groups or atoms represented by D are oxygen or sulfur, or a group of the formula $>N-R$; and that when each residue $R_2$ is hydrogen, a hydrocarbon residue, or alkoxycarbonyl, and X is a nitrogen atom, one of these two residues or atoms represented by D is an oxygen or sulfur atom, and the other residue is an oxygen atom or a group of the formula $>N-R$; and m, n, and p each independently is an integer of 0 to 5;

diphosphonic acids of Formula VIII

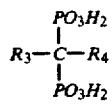

(VIII)

wherein $R_3$ and $R_4$ are identical or different and each is hydrogen, alkyl of 1–4 carbon atoms (straight chain or branched), halogen (Cl) hydroxy, amino ($NH_2$), or $-CH_2-COOH$; and the aminopolycarboxylic acids of Fromula IX

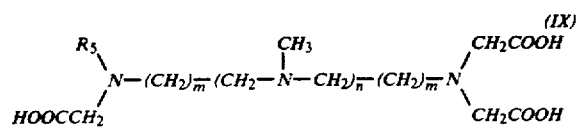

(IX)

wherein m is an integer of 1 to 4;

n is an integer of 0 to 2, and $R_5$ is a saturated or unsaturated hydrocarbon residue of 4–12 carbon atoms or the group $-CH_2-COOH$.

DETAILED DISCUSSION

Suitable amines of Formula VI for complex formation include, for example, ethylenediamine, diethylenetriamine, triethylenetetramine, tetraethylenepentamine, and pentaethylenehexamine. $R_1$ and $R_1'$ are preferably both H. Suitable alkyl groups $R_1$ and $R_1'$ are branched or straight chain.

Suitable hydrocarbon residues as A to D in Formulae VII and VIIa preferably are straight-chain or branched alkylene or alkenylene moieties of 2–8 carbon atoms, such as ethylene, propylene, butylene, and hexylene and their unsaturated analogs; cycloalkylene and cycloalkenylene residues of 3–8 C-atoms, such as cyclopropylene, cyclobutylene, cyclohexylene, and cycloheptylene and their unsaturated analogs; as well as aromatic residues, such as phenylene.

Suitable $R_2$ and R hydrocarbon groups include, preferably, straight-chain or branched alkyl or alkenyl residues of 1–8 carbon atoms, or cycloalkyl, aralkyl, and aryl groups each of 3–12 carbon atoms. Such hydrocarbon groups, having 4–12 C-atoms, and their unsaturated counterparts where appropriate, are suitable $R_5$ groups for Formula IX, e.g., $C_{4-12}$-alkyl, $C_{4-12}$-alkenyl, $C_{4-12}$-cycloalkyl, $C_{4-12}$-cycloalkenyl, $C_{7-12}$-hydrocarbon aralkyl, $C_{8-12}$-hydrocarbon aralkenyl, or $C_{6-12}$-hydrocarbonaryl.

Suitable alkoxycarbonyl residues for $R_2$, preferably are those of up to 10 carbon atoms.

Especially preferred compounds of Formula VII are macrocyclic complexing agents containing nitrogen and oxygen, such as, for example 5,6-benzo-4,7,13,16,21,24-hexaoxa-1,10-diazabicyclo[8.8.8]hexacosane, 1,7,10,16-tetra-4,13-diazacyclooctadecane, and 4,7,13,16,21,24-hexaoxa-1,10-diazabicyclo[8.8.8.]hexacosane.

Suitable diphosphonic acid complexing agents of Formula VIII, especially include ethane-1-hydroxy-1,1-diphosphonic acid, methanediphosphonic acid, and ethane-1-amino-1,1-diphosphonic acid.

If necessary or desirable, it is also possible to link the complex compounds of this invention to biomolecules, e.g., in order to change their pharmacokinetics, e.g., to transport the complex ions to specific sites in the living organism. Examples of suitable such biomolecules are immunoglobulins, hormones, such as insulin, glucagon, prostaglandins, steroid hormones, proteins, peptides, amino sugars, lipids, etc.

The coupling of the paramagnetic complex salts to the desired biomolecules is effected according to fully conventional methods known per se, for example by reacting the nucleophilic group of a biomolecule, such as an amino, phenol, sulfhydryl, or imidazole group, with an activated derivative of the complex compound. Examples of suitable activated derivatives include acid chlorides, mixed anhydrides (producible from the carboxy derivative of the complex compound with chlorocarbonic acid ester), activated esters, nitrenes, isothiocyanates, and the like. It is also possible to react an activated derivative of the biomolecule with a nucleophilic derivative of the complex compound.

Suitable acids for salt formation with the complexes include inorganic acids, such as, for example, hydrochloric acid and sulfuric acid, as well as organic acids, such as, for example, acetic acid, citric acid, aspartic acid, glutamic acid, etc., the resultant salts, of course being physiologically compatible.

Suitable bases for salt formation with the complexes include inorganic bases, e.g. sodium hydroxide, and organic bases, e.g. primary, secondary, or tertiary amines, especially glucamine, N-methylglucamine, N,N-dimethylglucamine, ethanolamine, diethanolamine, morpholine, etc., N-methylglucamine being preferred. Also suitable for salt formation are basic amino acids, such as, for example, lysine, ornithine, arginine, etc.

Where more than one form of a complex is possible, all are included within the scope of this invention.

The novel agents can be prepared conventionally by dissolving the paramagnetic salt in water or, e.g., a physiological saline solution, together with additives customary in galenic pharmacy, such as sodium chloride and/or stabilizers, and/or physiologically compatible buffer solutions (for instance, sodium dihydrogen phosphate solution), etc., and the solution is sterilized. The mixture is then conventionally formulated into a form suitable, e.g., for oral, neural or especially intravasal administration. If suspensions of the paramagnetic complex salts in water or a physiological saline solution should be particularly desired, e.g., for the purpose of oral administration, then the paramagnetic complex salt is mixed with one or more conventional adjuvant substances and/or tensides and/or flavoring agents to influence taste, all of which are known in the pharmacopeia. It is suspended in water or physiological saline solution before being administered orally. Preferably, from 3 to 10 g of paramagnetic complex salt and from 2 to 8 g of one or more adjuvant substances are used. Suitable adjuvant substances include saccharose, highly dispersed silicon dioxide, polyoxyethylene polyoxypropylene polymers, starch, magnesium stearate, sodium lauryl sulfate, talcum, lactose, carboxymethylcellulose-sodium and the like. The fully conventional considerations and techniques normally used in the preparation of other related diagnostic agents in general apply here.

For NMR diagnostics for administration to human patients, aqueous solutions can be employed containing 5–250 mmol/l, preferably 50–200 mmol/l of a paramagnetic complex salt of this invention. The aqueous solutions are generally in a pH range of about 6.5–8.0, preferably 6.5–7.5.

Because of the complex formation according to the present invention, the paramagnetic salts are detoxified; furthermore, the objective is achieved that the salts be stable and well soluble in water, even in the physiological pH range.

Complex salt solutions appear to be particularly suitable for improved imaging, demarcation and/or localization of lesions of the pancreas and of the liver, as well as of tumors and hemorrhages in the cranial area. In order to diagnose the location to be investigated, an aqueous solution, isotonic with respect to the blood, of a paramagnetic complex salt(s) is administered, for example, in a dosage of 1–100 μmol/kg intravenously. With a complex salt concentration of 50–200 mmol/l, about 1–50 ml of solution is generally required for the examination of a human patient. Adequate absorption of the paramagnetic complex salt by the tissue of interest takes place in about 15–60 minutes after intravenous administration of the aqueous solution. Thereafter, conventional NMR imaging is effected.

The maintenance and effectiveness of paramagnetism in the complex salts of this invention have been demonstrated in experiments on rats. a markedly greater change of the signal, as compared with the blank image, could be observed in the region of the liver parenchyma in the scanner, with a magnetic field of 0.15 tesla at a supplied energy of 300 watt/pulse and a 180° pulse of 720 μs with imaging times of 2 minutes, in each case 10 minutes after intravenous injection of 20 μmol/kg of manganese edetate as an aqueous methylglucamine salt solution of a concentration of 6 mmol/l. Only a comparatively minor contrasting could be attained under the same test conditions with an aqueous manganese (II) chloride solution.

As mentioned, by complex formation, the desired detoxification of the otherwise toxic paramagnetic salts is simultaneously achieved. This has been demonstrated, for example, in rats, where an $LD_{50}$ of 4 mmol/kg was determined after intravenous injection of an aqueous solution of the N-methylglucamine salt of manganese edetate. In contrast, manganese chloride showed, under identical conditions in rats, an $LD_{50}$ of merely 0.5 mmol/kg.

Many of the paramagnetic complexes of this invention are novel, e.g., the physiologically compatible complex salts of aminopolycarboxylic acids of Formulae I through V or diphosphonic acids of Formula VIII, and of the ions of the lanthanide elements of atomic numbers 57–70 or the ions of the transition metals of atomic numbers 21–29, 42, and 44, and optionally an organic base, such as di-N-methylglucamine salt of the manganese(II) complex of ethylenediaminetetraacetic acid, di-N-methylglucamine salt of the nickel(II) complex of ethylenediaminetetraacetic acid, diethanolamine salt of the cobalt(II) complex of ethylenediaminetetraacetic acid, dimorpholine salt of the manganese(II) complex of ethylenediaminetetraacetic acid, di-diethanolamine salt of the copper(II) complex of ethylenediaminetetraacetic acid, tri-diethanolamine salt of the manganese(II) complex of diethylenetriaminepentaacetic acid, tri-N-methylglucamine salt of the manganese(II) complex of diethylenetriaminepentaacetic acid, N-methylglucamine salt of the gadolinium(III) complex of ethylenediaminetetraacetic acid, N-methylglucamine salt of the dysprosium(III) complex of ethylenediaminetetraacetic acid, di-N-methylglucamine salt of the gadolinium(III) complex of diethylenetriaminepentaacetic acid, di-lysine salt of the gadolinium(III) complex of diethylenetriaminepentaacetic acid, di-N-methylglucamine salt of the holmium(III) complex of diethylenetriaminepentaacetic acid, and N-methylglucamine salt of the iron(II) complex of ethane-1-hydroxy-1,1-diphosphonic acid.

All of the complex salts of this invention can be readily and conventionally prepared using standard methods for preparation of such compounds. For example, they may be conventionally prepared by dissolving a compound yielding the cation, such as, for example, a halide, e.g., manganese chloride, gadolinium chloride or other lanthanide or transition metal halide; a solubilizing medium such as water and/or alcohol, such as methanol, ethanol, etc., and stirring with the corresponding quantity of the desired complexing agent, optionally while heating to 50°–120° C. until the reaction is completed. If the thus-formed complex is insoluble in the solvent utilized, a crystallized product evolves which can be conventionally filtered off and worked up. If the complex is soluble in the solvent employed, it can be isolated by evaporating the solution to dryness and worked up.

When a salt with an inorganic or organic acid or base is desired, and one or more acids or basic groups are still present in the paramagnetic complex obtained, the resultant complex compound can be subsequently dissolved or suspended in water and combined with the desired inorganic or organic base or acid until the neutral point is reached. After filtration from the undissolved proportions, the solution is evaporated and the desired complex salt is obtained as the residue.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1A

The following example will explain in greater detail the conductance of an NMR diagnostic investigation using a complex salt of this invention.

A sterile, aqueous solution of the N-methylglucamine salt of the gadolinium(III) complex of diethylenetriaminepentaacetic acid is prepared at a concentration of 0.1 mol/l. The pH of the clear solution is 7.2.

The whole-body scanner utilized for NMR tomography (Siemens AG, Erlangen [West Germany]) operates with a magnetic field of 0.1 tesla corresponding to a Larmor proton frequency of 4.99 MHz. The device was equipped with a high-frequency transmitting and receiving coil of relatively small dimensions to be able to reproduce even objects of relatively small size with satisfactory resolution. The studies were performed using the spin-echo technique. The time of imaging was between 1 and 3 minutes.

The experiments are performed with male rats of the Wistar-Han-Schering (SPF) strain having a body weight of 250 g. Eight days prior to the test, the animals receive intraperitoneally a Novikoff hepatoma tumor cell suspension (0.5 ml with $1 \times 10^6$ cell). The animals are anesthesized by intraperitoneal injection of sodium pentobarbital (60 mg/kg body weight). Subsequently, a winged cannula is inserted in one of the tail veins of the animals. Before administration of the contrast medium, images are prepared in sagittal and horizontal planes of the trunk of the body.

The contrast medium is administered intravenously within one minute in a dose of 1 mmol/kg.

Images taken between 22 and 25 minutes after administration, show a vigorous increase in brightening in the abdomen. After intravenous administration, the contrast medium passes into the pathological fluid accumulations and there effects a strong shortening of the spin-lattice relaxation time ($T_1$) leading to an increase in signal intensity. Only after administration of the contrast medium is it possible to discern the tumorous fluid accumulation and an improved demarcation of the organs. Without the presence of contrast medium, hardly any structures can be recognized in the abdomen since the organs show only minor differences in proton density and relaxation times.

The structural contrast is likewise improved upon the oral administration of the contrast agent. For this purpose, 5 ml of the N-methylglucamine salt solution of the gadolinium complex of diethylenetriaminepentaacetic acid is administered, in a concentration of 1 mmol/l using a catheter, to an anesthetized male rat (body weight: 250 g). Only after administration of the contrast medium is it possible to discern a clear demarcation of the stomach and of the intestinal tract, respectively, from the remainder of the organs.

In-house pharmacokinetic studies on rats have shown that the N-methylglucamine salt of the gadolinium complex of diethylenetriaminepentaacetic acid, upon intravenous and subcutaneous administration, is quite predominantly eliminated renally within 24 hours. The gadolinium complex is excreted by glomerular filtration by rats with a half-life value of about 20 minutes. The proportion eliminated with the feces is smaller than 5% of the dose administered.

No absorption of the compound is observed upon oral administration. The pharmacokinetic behavior is similar to that of the classical X-ray contrast media for uroangiography.

EXAMPLE 1B

Preparation of the Manganese-II Complex of Ethylenediamine Tetraacetic Acid:

A suspension of 6.17 g of manganese-II carbonate in 500 ml of water is mixed with 14.6 g of ethylenediamine tetraacetic acid and heated on a vapor bath, while being stirred, during the course of which gas is generated. The initially pink color disappears after approximately 20 minutes and except for a small residue, everything enters solution. After being stirred for one hour at 110° C., the undissolved material is filtered off, and the filtrate is cooled. After standing for 15 hours, the crystallizate is aspirated off and dried:

Yield=14.1 g (molecular weight: 345.17) Freezing point: 256°/258°–259° C.

EXAMPLE 1C

Preparation of the Gadolinium-III Complex of Diethylenetriamine Pentaacetic Acid:

A suspension of 435 g of gadolinium oxide ($Gd_2O_3$) and 944 g of diethylenetriamine pentaacetic acid in 12 l of water is heated, while being stirred, to 90° C. to 100° C. and stirred at this temperature for 48 hours. The undissolved material is then filtered off, and the filtrate is evaporated until dry. The amorphous residue is pulverized.

Yield: 144 g (molecular weight: 547.58);

Freezing point: melts beyond 235° and remains undecomposed up to 320° C.

EXAMPLE 1

Preparation of Di-N-methylglucamine Salt of the Manganese(II) Complex of Ethylenediaminetetraacetic Acid, $C_{24}H_{48}N_4O_{18}Mn$ A suspension is prepared from 7.4 g (=20 mmol) of the manganese(II) complex of ethylenediaminetetraacetic acid (water content: 6.9%) and 30 ml of water, and the compound is dissolved by adding about 7.8 g (=about 40 mmol) of N-methylglucamine at pH 7.5. After filtration of a small amount of undissolved material, the solution is concentrated to dryness under vacuum. A solid foam is produced in quantitative yield, melting starting with 95° C. and becoming a viscous fluid at 170° C.

Dissolution in hot ethanol and concentration under vacuum to dryness yields the compound as a white, hygroscopic powder.

The following compounds are obtained analogously:

di-N-methylglucamine salt of nickel(II) complex of ethylenediaminetetraacetic acid, $C_{24}H_{48}N_4O_{18}Ni$, as a blue powder;

diethanolamine salt of cobalt(II) complex of ethylenediaminetetraacetic acid, $C_{14}H_{28}N_4O_{10}Co$, as a pink-colored powder;

dimorpholine salt of manganese(II) complex of ethylenediaminetetraacetic acid, $C_{18}H_{32}N_4O_{10}MN$, as a white powder;

di-diethanolamine salt of copper(II) complex of ethylenediaminetetraacetic acid, $C_{18}H_{36}N_4O_{12}Cu$ as a blue powder;

tri-diethanolamine salt of manganese(II) complex of diethylenetriaminepentaacetic acid, $C_{26}H_{54}N_6O_{16}Mn$, as a yellow powder;

tri-N-methylglucamine salt of manganese(II) complex of diethylenetriaminepentaacetic acid, $C_{35}H_{72}N_6O_{25}Mn$, as a white powder.

EXAMPLE 2

Preparation of N-Methylglucamine Salt of the Gadolinium(III) Complex of Ethylenediaminetetraacetic Acid, $C_{17}H_{30}N_3O_{13}Gd$ 4.58 g (=10 mmol) of the gadolinium(III) complex of ethylenediaminetetraacetic acid (water content: 2.7%) is suspended in 15 ml of water and dissolved by adding 1.95 g (=10 mmol) of N-methylglucamine at pH 7.4. The solution is filtered and then concentrated to dryness under vacuum, thus obtaining a solid foam. The yield is practically quantitative, considering the water content of 8.5%. The compound sinters starting with 90° C.; foam evolves from 140° C. on.

The compound is obtained as a white powder by dissolving in hot ethanol and concentration to dryness under vacuum.

The following compounds are obtained analogously: N-methylglucamine salt of dysprosium(III) complex of ethylenediaminetetraacetic acid, $C_{17}H_{30}N_3O_{13}Dy$; di-N-methylglucamine salt of holmium(III) complex of diethylenetriaminepentaacetic acid, $C_{28}H_{54}N_5O_{20}Ho$. di-lysine salt of the gadolinium(III) complex of diethylenetriaminepentaacetic acid, $C_{26}H_{28}N_7O_{14}Gd$; di-N-methylglucamine salt of the gadolinium(III) complex of diethylenetriaminepentaacetic acid, $C_{28}H_{54}N_5O_{20}Gd$.

EXAMPLE 3

Preparation of Solution of the Di-N-methylglucamine Salt of the Manganese(II) Complex of Ethylenediaminetetraacetic Acid 3.68 g (=5 mmol) of the compound described in Example 1 is dissolved in 70 ml of water pro injectione (p.i.), and the solution is combined with 0.4 g of sodium chloride. Subsequently the mixture is replenished to 100 ml with water p.i., and the solution is dispensed into ampoules through a sterile filter. The solution is blood-isotonic with 280 mOsm.

EXAMPLE 4

Preparation of a Solution of the N-Methylglucamine Salt of the Gadolinium(III) Complex of Ethylenedimainetetraacetic Acid 9.63 g (=15 mmol) of the compound disclosed in Example 2 is dissolved in 100 ml of water p.i. The approximately blood-isotonic solution is dispensed into ampoules through a sterile filter.

EXAMPLE 5

Preparation of a Solution of the Di-N-methylglucamine Salt of the Gadolinium(III) Complex of Diethylenetriaminepentaacetic Acid 5.35 g (=9 mmol) of the gadolinium(III) complex of diethylenetriaminepentaacetic acid (water content 8%) is dissolved in 50 ml of water p.i. and neutralized by adding about 3.2 g (corresponding to about 18 mmol) of N-methylglucamine to pH 7.5. Subsequently the solution is replenished with water p.i. to 100 ml, dispensed into ampoules, and heat-sterilized. The concentration of the solution is set to blood isotonia (about 280 mOsm).

EXAMPLE 6

Preparation of a Solution of the Di-N-methylglucamine Salt of the Dysprosium(III) Complex of Diethylenetriaminepentaacetic Acid 8.00 g (=15 mmol) of the dysprosium(III) complex of diethylenetriaminepentaacetic acid is dissolved in 80 ml of water p.i. with the addition of about 5.3 g (corresponding to about 30 mmol) of N-methylglucamine at pH 7.5. The solution is then replenished with water p.i. to 170 ml. The approximately blood-isotonic solution is filled into ampoules and heat-sterilized.

EXAMPLE 7

Preparation of a Solution of the Di-N-methylglucamine Salt of the Holmium(III) Complex of Diethylenetriaminepentaacetic Acid 8.02 g (=15 mmol) of the holmium(III) complex of diethylenetriaminepentaacetic acid is dissolved in 80 ml of water p.i. with the addition of about 5.3 g (corresponding to about 30 mmol) of N-methylglucamine at pH 7.2. Then the solution is replenished to 170 ml with water p.i. The approximately blood-isotonic solution is dispensed into ampoules and heat-sterilized.

The solution can also be produced by dissolving the complex salt isolated according to Example 2 in water p.i.

EXAMPLE 8

Preparation of a Solution of the Disodium Salt of the Manganese(II) Complex of Ethylenediaminetetraacetic Acid 5.55 g (=15 mmol) of the manganese(II) complex of ethylenediaminetetraacetic acid (water content: 6.9%) is dissolved in 80 ml of water p.i. with the addition of dilute sodium hydroxide solution at pH 7.5. Subsequently the solution is replenished with water p.i. to 170 ml, filled into ampoules under filtration, and heat-sterilized.

EXAMPLE 9

Preparation of a Solution of the N-methylglucamine Salt of the Iron(II) Complex of Ethane-1-hydroxy-1,1-diphosphonic Acid 1.27 g (=10 mmol) of iron(II) chloride is dissolved in 8.8 ml of methanol, and the solution is combined with 3.2 ml of a 60% by weight solution of ethane-1-hydroxy-1,1-diphosphonic acid in water. The solution is concentrated to dryness under vacuum, and the residue is washed three times with anhydrous methanol. After drying, the residue is taken up in 50 ml of water p.i. and dissolved by adding about 1.8 g (corresponding to about 10 mmol) of N-methylglucamine at pH 7.5. The solution is thereafter replenished to 100 ml with water p.i. and dispensed into ampoules after sterile filtration.

EXAMPLE 10

Preparation of a Solution of the Complex $[Ni_2(C_6H_{18}N_4)_3]Cl_4 \cdot 2 H_2O$ 3.58 g (=5 mmol) of the nickel(II) chloride triethylenetetramine complex is dissolved in 80 ml of water p.i. with the addition of dilute hydrochloric acid p.a. at pH 7.6. The solution is then replenished with water p.i. to 100 ml. After filtration through a sterile filter, the solution is filled into ampoules.

EXAMPLE 11

*Preparation of a Solution of the Copper(II) Chloride Complex of 4,7,13,16,21,24-Hexaoxa-1,10-diazabicyclo[8.8.8]hexacosane*

2.55 g (=5 mmol) of the complex obtained from copper-(II) chloride and 4,7,13,16,21,24-hexaoxa-1,10-diazabicyclo[8.8.8]hexacosane is dissolved in 80 ml of water p.i. with the addition of dilute hydrochloric acid p.a. at pH 7.3, and the solution is thereafter filled up to 100 ml with water p.i. After sterile filtration, the solution is dispensed into ampoules.

EXAMPLE 12

*Preparation of the Manganese Complex Salt with Diethylenetriamine [Mn(C₄H₁₃N₃)₂]Cl₂*

A solution of 3.94 g of manganese(II) chloride in 200 ml of ethanol (95% strength) is combined dropwise under agitation with a solution of 41.2 g of diethylenetriamine in 100 ml of 50% ethyl alcohol, the temperature rising to 42° C. The initially formed precipitate redissolves after some time. After 15 hours of stirring at room temperature, the solution is concentrated, thus obtaining 70 g of a crude product which is heated to boiling with 350 ml of ethanol for 30 minutes. The product is then vacuum-filtered in the hot state, washed with ethanol, and dried, thus obtaining 57 g of a crude product which is recrystallized from 400 ml of methanol over carbon. Yield: 40 g (60% of theory).

EXAMPLE 13

*Preparation of a Solution of the N-Methylglucamine Salt of the Manganese(II) Complex of N,N,N'-Tri(carboxymethyl)-N'-benzylethylenediamine*

Analogously to Example 6, 5.65 g (=15 mmol) of the manganese(II) complex of N,N,N'-tris(carboxymethyl)-N'-benzylethylenediamine is dissolved in 80 ml of water (pro injectione) with the addition of about 2.93 g (approximately 20 mmol) of N-methylglucamine at pH 7.5. The solution is thereafter filled up to 170 ml with water (pro injectione). The approximately blood-isotonic solution is filled into ampoules and sterilized.

EXAMPLE 14

*Preparation of a Solution of the N-Methylglucamine Salt of the Gadolinium(III) Complex of Bis[2-(biscarboxymethylamino)ethyl]methylamine*

Following the mode of operation described in Example 6, a ready-for-use solution is produced from 7.55 g (approximately 15 mmol) of the gadolinium(III) complex of bis[2-(biscarboxymethylamino)ethyl]methylamine and 2.93 g (approximately 15 mmol) of N-methylglucamine.

EXAMPLE 15

*Preparation of a Solution of the Di-N-methylglucamine Salt of the Manganese(II) Complex of Hexanediyliminotetraacetic Acid*

Analogously to the procedure disclosed in Example 6, 6.02 g (approximately 15 mmol) of manganese(II)complex of hexanediyldiaminetetraacetic acid and 5.86 g (approximately 30 mmol) of N-methylglucamine yield a ready-for-use solution.

EXAMPLE 16

*(Composition of a powder for preparing a suspension)*

4.000 g gadolinium-III complex of the diethylaminetriamine pentaacetic acid (water content 8%)
3.895 g saccharose
0.100 g polyoxyethylene polyoxypropylene polymers
0.005 g flavorings
8.000 g The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

AS A RESULT OF REEXAMINATION, IT HAS BEEN DETERMINED THAT:

The patentability of claims 1–57, 59–163 and 165–169 is confirmed.

Claims 58 and 164 are determined to be patentable as amended.

New claims 170–249 are added and determined to be patentable.

58. A method of claim [1] *2*, wherein the paramagnetic ion is chelated by an open-chain chelating agent.

164. A method of claim [133] *134*, wherein the chelate complex is nonionic.

*170. A method according to claim 13, wherein said agent contains 5–250 mmole/l of said chelate complex.*

*171. A method according to claim 13, wherein said agent has a pH of 6.5–8.0.*

*172. A method according to claim 13, wherein administration is oral.*

*173. A method according to claim 13, wherein administration is neural.*

*174. A method according to claim 13, wherein administration is intravascular.*

*175. A method according to claim 13, wherein said agent is isotonic with respect to blood.*

*176. A method according to claim 13, wherein said agent is an aqueous solution.*

*177. A method according to claim 13, wherein said chelate complex is water soluble.*

*178. A method according to claim 13, wherein said chelate complex is intravenously administered in a dose of 1–100 μmole/kg.*

*179. A method according to claim 13, wherein said chelate complex is intravenously administered in a dose of 1 μmole/kg–1 mmole/kg.*

*180. A method according to claim 134, wherein said agent contains 5–250 mmole/l of said chelate complex.*

*181. A method according to claim 134, wherein said agent has a pH of 6.5–8.0.*

*182. A method according to claim 134, wherein administration is oral.*

*183. A method according to claim 134, wherein administration is neural.*

*184. A method according to claim 134, wherein administration is intravascular.*

*185. A method according to claim 134, wherein said agent is isotonic with respect to blood.*

*186. A method according to claim 134, wherein said agent is an aqueous solution.*

187. A method according to claim 134, wherein said chelate complex is water soluble.

188. A method according to claim 134, wherein said chelate complex is intravenously administered in a dose of 1-100 μmole/kg.

189. A method according to claim 134, wherein said chelate complex is intravenously administered in a dose of 1 μmole/kg-1 mmole/kg.

190. A method according to claim 155, wherein said agent contains 5-250 mmole/l of said chelate complex.

191. A method according to claim 155, wherein said agent has a pH of 6.5-8.0.

192. A method according to claim 155, wherein administration is oral.

193. A method according to claim 155, wherein administration is neural.

194. A method according to claim 155, wherein administration is intravascular.

195. A method according to claim 155, wherein said agent is isotonic with respect to blood.

196. A method according to claim 155, wherein said agent is an aqueous solution.

197. A method according to claim 155, wherein said chelate complex is water soluble.

198. A method according to claim 155, wherein said chelate complex is intravenously administered in a dose of 1-100 μmole/kg.

199. A method according to claim 155, wherein said chelate complex is intravenously administered in a dose of 1 μmole/kg-1 mmole/kg.

200. A method according to claim 164, wherein said agent contains 5-250 mmole/l of said chelate complex.

201. A method according to claim 164, wherein said agent has a pH of 6.5-8.0.

202. A method according to claim 164, wherein administration is oral.

203. A method according to claim 164, wherein administration is neural.

204. A method according to claim 164, wherein administration is intravascular.

205. A method according to claim 164, wherein said agent is isotonic with respect to blood.

206. A method according to claim 164, wherein said agent is an aqueous solution.

207. A method according to claim 164, wherein said chelate complex is water soluble.

208. A method according to claim 164, wherein said chelate complex is intravenously administered in a dose of 1-100 μmole/kg.

209. A method according to claim 164, wherein said chelate complex is intravenously administered in a dose of 1 μmole/kg-1 mmole/kg.

210. A method according to claim 23, wherein said agent contains 5-250 mmole/l of said chelate complex.

211. A method according to claim 23, wherein said agent has a pH of 6.5-8.0.

212. A method according to claim 23, wherein administration is oral.

213. A method according to claim 23, wherein administration is neural.

214. A method according to claim 23, wherein administration is intravascular.

215. A method according to claim 23, wherein said agent is isotonic with respect to blood.

216. A method according to claim 23, wherein said agent is an aqueous solution.

217. A method according to claim 23, wherein said chelate complex is water soluble.

218. A method according to claim 23, wherein said chelate complex is intravenously administered in a dose of 1-100 μmole/kg.

219. A method according to claim 23, wherein said chelate complex is intravenously administered in a dose of 1 μmole/kg-1 mmole/kg.

220. A method according to claim 137, wherein said agent contains 5-250 mmole/l of said chelate complex.

221. A method according to claim 137, wherein said agent has a pH of 6.5-8.0.

222. A method according to claim 137, wherein administration is oral.

223. A method according to claim 137, wherein administration is neural.

224. A method according to claim 137, wherein administration is intravascular.

225. A method according to claim 137, wherein said agent is isotonic with respect to blood.

226. A method according to claim 137, wherein said agent is an aqueous solution.

227. A method according to claim 137, wherein said chelate complex is water soluble.

228. A method according to claim 137, wherein said chelate complex is intravenously administered in a dose of 1-100 μmole/kg.

229. A method according to claim 137, wherein said chelate complex is intravenously administered in a dose of 1 μmole/kg-1 mmole/kg.

230. A method according to claim 157, wherein said agent contains 5-250 mmole/l of said chelate complex.

231. A method according to claim 157, wherein said agent has a pH of 6.5-8.0.

232. A method according to claim 157, wherein administration is oral.

233. A method according to claim 157, wherein administration is neural.

234. A method according to claim 157, wherein administration is intravascular.

235. A method according to claim 157, wherein said agent is isotonic with respect to blood.

236. A method according to claim 157, wherein said agent is an aqueous solution.

237. A method according to claim 157, wherein said chelate complex is water soluble.

238. A method according to claim 157, wherein said chelate complex is intravenously administered in a dose of 1-100 μmole/kg.

239. A method according to claim 157, wherein said chelate complex is intravenously administered in a dose of 1 μmole/kg-1 mmole/kg.

240. A method according to claim 165, wherein said agent contains 5-250 mmole/l of said chelate complex.

241. A method according to claim 165, wherein said agent has a pH of 6.5-8.0.

242. A method according to claim 165, wherein administration is oral.

243. A method according to claim 165, wherein administration is neural.

244. A method according to claim 165, wherein administration is intravascular.

245. A method according to claim 165, wherein said agent is isotonic with respect to blood.

246. A method according to claim 165, wherein said agent is an aqueous solution.

247. A method according to claim 165, wherein said chelate complex is water soluble.

248. A method according to claim 165, wherein said chelate complex is intravenously administered in a dose of 1-100 μmole/kg.

249. A method according to claim 165, wherein said chelate complex is intravenously administered in a dose of 1 μmole/kg-1 mmole/kg.

* * * * *